US011666664B2

(12) United States Patent
Elmaleh et al.

(10) Patent No.: US 11,666,664 B2
(45) Date of Patent: Jun. 6, 2023

(54) SELF ASSEMBLING MOLECULES FOR TARGETED DRUG DELIVERY

(71) Applicant: The General Hospital Corporation, Boston, MA (US)

(72) Inventors: David R. Elmaleh, Newton, MA (US); Kazue Takahashi, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 240 days.

(21) Appl. No.: 16/694,437

(22) Filed: Nov. 25, 2019

(65) Prior Publication Data
US 2020/0078472 A1 Mar. 12, 2020

Related U.S. Application Data

(63) Continuation of application No. 15/563,339, filed as application No. PCT/US2016/025290 on Mar. 31, 2016, now abandoned.

(60) Provisional application No. 62/140,696, filed on Mar. 31, 2015.

(51) Int. Cl.
| | | |
|---|---|---|
| A61K 39/00 | (2006.01) | |
| C07K 16/00 | (2006.01) | |
| A61K 47/69 | (2017.01) | |
| A61K 9/51 | (2006.01) | |
| A61K 47/62 | (2017.01) | |
| A61K 47/68 | (2017.01) | |
| A61P 35/00 | (2006.01) | |
| A61K 9/50 | (2006.01) | |
| A61K 31/337 | (2006.01) | |
| A61K 31/473 | (2006.01) | |
| A61K 31/7068 | (2006.01) | |
| A61K 39/39 | (2006.01) | |
| A61K 49/00 | (2006.01) | |
| A61K 49/18 | (2006.01) | |
| A61K 51/12 | (2006.01) | |

(52) U.S. Cl.
CPC ........ *A61K 47/6949* (2017.08); *A61K 9/5052* (2013.01); *A61K 9/5169* (2013.01); *A61K 31/337* (2013.01); *A61K 31/473* (2013.01); *A61K 31/7068* (2013.01); *A61K 39/39* (2013.01); *A61K 47/62* (2017.08); *A61K 47/6849* (2017.08); *A61K 47/6925* (2017.08); *A61K 49/0069* (2013.01); *A61K 49/0091* (2013.01); *A61K 49/189* (2013.01); *A61K 49/1821* (2013.01); *A61K 51/1251* (2013.01); *A61K 51/1268* (2013.01); *A61P 35/00* (2018.01)

(58) Field of Classification Search
CPC .. A61K 47/6949; A61K 31/473; A61K 39/39; A61K 47/62; A61K 47/6849; A61K 47/6925
See application file for complete search history.

(56) References Cited

U.S. PATENT DOCUMENTS

| | | |
|---|---|---|
| 2003/0049203 A1 | 3/2003 | Elmaleh et al. |
| 2007/0141163 A1 | 6/2007 | Vitaliano et al. |
| 2009/0035389 A1 | 2/2009 | Campion et al. |
| 2010/0226856 A1* | 9/2010 | Vitaliano ............... A61K 47/42 424/9.1 |
| 2016/0159905 A1 | 6/2016 | Abdiche et al. |
| 2018/0140719 A1 | 5/2018 | Elmaleh et al. |

FOREIGN PATENT DOCUMENTS

| | | |
|---|---|---|
| JP | 2006340714 A | 12/2006 |
| WO | WO-2007/073932 A2 | 7/2007 |
| WO | WO2008/103920 * | 8/2008 |
| WO | WO-2008103920 A3 | 11/2008 |
| WO | WO-2010101694 A1 | 9/2010 |
| WO | WO-2014/141289 A1 | 9/2014 |
| WO | WO-2015/108783 A1 | 7/2015 |

OTHER PUBLICATIONS

Extended European Search Report received for EP Patent Application No. EP16774208, dated Oct. 25, 2018.
Falvo et al., "Antibody-drug conjugates: targeting melanoma with cisplatin encapsulated in protein-cage nanoparticles based on human ferritin," Nanoscale, 5(24):12278-12285 (2013).
Flenniken et al., "A library of protein cage architectures as nanomaterials," Curr Top Microbiol Immunol, 327:71-93 (2009).
International Search Report and Written Opinion for International Application No. PCT/US2016/025290 dated Jul. 11, 2016.
Extended European Search Report for EP Application No. 21178644 dated Dec. 10, 2021.
Niu et al., "Cloning of cDNAs for H1FO, TOP1, Clta, and CDK1 and the effects of cryopreservation on the expression of their mRNA transcripts in yak (*Bos grunniens*) oocytes," Cryobiol, 69(1): 55-60 (2014).

(Continued)

*Primary Examiner* — Lei Yao

(74) *Attorney, Agent, or Firm* — Foley Hoag LLP; Janine S. Ladislaw; Allison L. Gilder

(57) ABSTRACT

Described herein are self-assembling protein molecules for delivering a payload, for example, a toxic anti-cancer agent, a cancer immunotherapy, a toxic anti-cancer agent and a cancer immunotherapy, or an imaging agent, to specific tissues. Examples of self-assembled proteins include clathrin and derivatives of clathrin.

8 Claims, 4 Drawing Sheets
Specification includes a Sequence Listing.

(56) References Cited

OTHER PUBLICATIONS

Zaki et al., "Gateways for the intracellular access of nanocarriers: a review of receptor-mediated endocytosis mechanisms and of strategies in receptor targeting," Exp Opin Drug Deliv, 7(8): 895-913 (2010).
Brodsky., "Living with Clathrin: Its Role in Intracellular Membrane Traffic" Science, 242:1396-1402 (1988).
Reeck et al., "'Homology' in Proteins and Nucleic Acids: A Terminology Muddle and a Way out of it," Letter to the Editor, Cell 50(667): 1 page (1987).

\* cited by examiner

SEQUENCE LISTING

```
<160> NUMBER OF SEQ ID NOS: 9

<210> SEQ ID NO 1
<211> LENGTH: 1638
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Gln Ile Leu Pro Ile Arg Phe Gln Glu His Leu Gln Leu Gln
1               5                   10                  15

Asn Leu Gly Ile Asn Pro Ala Asn Ile Gly Phe Ser Thr Leu Thr Met
                20                  25                  30

Glu Ser Asp Lys Phe Ile Cys Ile Arg Glu Lys Val Gly Glu Gln Ala
            35                  40                  45

Gln Val Val Ile Ile Asp Met Asn Asp Pro Ser Asn Pro Ile Arg Arg
        50                  55                  60

Pro Ile Ser Ala Asp Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Thr Asp Asp Val Thr Phe Trp Lys
                100                 105                 110

Trp Ile Ser Leu Asn Thr Val Ala Leu Val Thr Asp Asn Ala Val Tyr
            115                 120                 125

His Trp Ser Met Glu Gly Glu Ser Gln Pro Val Lys Met Phe Asp Arg
        130                 135                 140

His Ser Ser Leu Ala Gly Cys Gln Ile Ile Asn Tyr Arg Thr Asp Ala
145                 150                 155                 160

Lys Gln Lys Trp Leu Leu Leu Thr Gly Ile Ser Ala Gln Gln Asn Arg
                165                 170                 175

Val Val Gly Ala Met Gln Leu Tyr Ser Val Asp Arg Lys Val Ser Gln
                180                 185                 190

Pro Ile Glu Gly His Ala Ala Ser Phe Ala Gln Phe Lys Met Glu Gly
            195                 200                 205

Asn Ala Glu Glu Ser Thr Leu Phe Cys Phe Ala Val Arg Gly Gln Ala
        210                 215                 220

Gly Gly Lys Leu His Ile Ile Glu Val Gly Thr Pro Pro Thr Gly Asn
225                 230                 235                 240
```

-continued

Gln Pro Phe Pro Lys Lys Ala Val Asp Val Phe Pro Pro Glu Ala
            245                 250                 255

Gln Asn Asp Phe Pro Val Ala Met Gln Ile Ser Glu Lys His Asp Val
        260                 265                 270

Val Phe Leu Ile Thr Lys Tyr Gly Tyr Ile His Leu Tyr Asp Leu Glu
    275                 280                 285

Thr Gly Thr Cys Ile Tyr Met Asn Arg Ile Ser Gly Glu Thr Ile Phe
290                 295                 300

Val Thr Ala Pro His Glu Ala Thr Ala Gly Ile Ile Gly Val Asn Arg
305                 310                 315                 320

Lys Gly Gln Val Leu Ser Val Cys Val Glu Glu Asn Ile Ile Pro
            325                 330                 335

Tyr Ile Thr Asn Val Leu Gln Asn Pro Asp Leu Ala Leu Arg Met Ala
            340                 345                 350

Val Arg Asn Asn Leu Ala Gly Ala Glu Leu Phe Ala Arg Lys Phe
        355                 360                 365

Asn Ala Leu Phe Ala Gln Gly Asn Tyr Ser Glu Ala Ala Lys Val Ala
    370                 375                 380

Ala Asn Ala Pro Lys Gly Ile Leu Arg Thr Pro Asp Thr Ile Arg Arg
385                 390                 395                 400

Phe Gln Ser Val Pro Ala Gln Pro Gly Gln Thr Ser Pro Leu Leu Gln
            405                 410                 415

Tyr Phe Gly Ile Leu Leu Asp Gln Gly Gln Leu Asn Lys Tyr Glu Ser
            420                 425                 430

Leu Glu Leu Cys Arg Pro Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Ser Val Asp Pro Thr Leu Ala Leu Ser Val Tyr Leu
465                 470                 475                 480

Arg Ala Asn Val Pro Asn Lys Val Ile Gln Cys Phe Ala Glu Thr Gly
            485                 490                 495

Gln Val Gln Lys Ile Val Leu Tyr Ala Lys Lys Val Gly Tyr Thr Pro
            500                 505                 510

Asp Trp Ile Phe Leu Leu Arg Asn Val Met Arg Ile Ser Pro Asp Gln
        515                 520                 525

Gly Gln Gln Phe Ala Gln Met Leu Val Gln Asp Glu Pro Leu Ala
    530                 535                 540

Asp Ile Thr Gln Ile Val Asp Val Phe Met Glu Tyr Asn Leu Ile Gln
545                 550                 555                 560

Gln Cys Thr Ala Phe Leu Leu Asp Ala Leu Lys Asn Asn Arg Pro Ser
            565                 570                 575

Glu Gly Pro Leu Gln Thr Arg Leu Leu Glu Met Asn Leu Met His Ala
            580                 585                 590

Pro Gln Val Ala Asp Ala Ile Leu Gly Asn Gln Met Phe Thr His Tyr
        595                 600                 605

Asp Arg Ala His Ile Ala Gln Leu Cys Glu Lys Ala Gly Leu Leu Gln
    610                 615                 620

Arg Ala Leu Glu His Phe Thr Asp Leu Tyr Asp Ile Lys Arg Ala Val
625                 630                 635                 640

Val His Thr His Leu Leu Asn Pro Glu Trp Leu Val Asn Tyr Phe Gly
            645                 650                 655

Ser Leu Ser Val Glu Asp Ser Leu Glu Cys Leu Arg Ala Met Leu Ser

```
                660               665               670
Ala Asn Ile Arg Gln Asn Leu Gln Ile Cys Val Gln Val Ala Ser Lys
            675               680               685

Tyr His Glu Gln Leu Ser Thr Gln Ser Leu Ile Glu Leu Phe Glu Ser
690               695               700

Phe Lys Ser Phe Glu Gly Leu Phe Tyr Phe Leu Gly Ser Ile Val Asn
705               710               715               720

Phe Ser Gln Asp Pro Asp Val His Phe Lys Tyr Ile Gln Ala Ala Cys
                725               730               735

Lys Thr Gly Gln Ile Lys Glu Val Glu Arg Ile Cys Arg Glu Ser Asn
                740               745               750

Cys Tyr Asp Pro Glu Arg Val Lys Asn Phe Leu Lys Glu Ala Lys Leu
            755               760               765

Thr Asp Gln Leu Pro Leu Ile Ile Val Cys Asp Arg Phe Asp Phe Val
770               775               780

His Asp Leu Val Leu Tyr Leu Tyr Arg Asn Asn Leu Gln Lys Tyr Ile
785               790               795               800

Glu Ile Tyr Val Gln Lys Val Asn Pro Ser Arg Leu Pro Val Val Ile
                805               810               815

Gly Gly Leu Leu Asp Val Asp Cys Ser Glu Asp Val Ile Lys Asn Leu
                820               825               830

Ile Leu Val Val Arg Gly Gln Phe Ser Thr Asp Glu Leu Val Ala Glu
            835               840               845

Val Glu Lys Arg Asn Arg Leu Lys Leu Leu Pro Trp Leu Glu Ala
850               855               860

Arg Ile His Glu Gly Cys Glu Glu Pro Ala Thr His Asn Ala Leu Ala
865               870               875               880

Lys Ile Tyr Ile Asp Ser Asn Asn Pro Glu Arg Phe Leu Arg Glu
                885               890               895

Asn Pro Tyr Tyr Asp Ser Arg Val Val Gly Lys Tyr Cys Glu Lys Arg
                900               905               910

Asp Pro His Leu Ala Cys Val Ala Tyr Glu Arg Gly Gln Cys Asp Leu
            915               920               925

Glu Leu Ile Asn Val Cys Asn Glu Asn Ser Leu Phe Lys Ser Leu Ser
930               935               940

Arg Tyr Leu Val Arg Arg Lys Asp Pro Glu Leu Trp Gly Ser Val Leu
945               950               955               960

Leu Glu Ser Asn Pro Tyr Arg Arg Pro Leu Ile Asp Gln Val Val Gln
                965               970               975

Thr Ala Leu Ser Glu Thr Gln Asp Pro Glu Glu Val Ser Val Thr Val
            980               985               990

Lys Ala Phe Met Thr Ala Asp Leu Pro Asn Glu Leu Ile Glu Leu Leu
            995               1000              1005

Glu Lys Ile Val Leu Asp Asn Ser Val Phe Ser Glu His Arg Asn
    1010              1015              1020

Leu Gln Asn Leu Leu Ile Leu Thr Ala Ile Lys Ala Asp Arg Thr
    1025              1030              1035

Arg Val Met Glu Tyr Ile Asn Arg Leu Asp Asn Tyr Asp Ala Pro
    1040              1045              1050

Asp Ile Ala Asn Ile Ala Ile Ser Asn Glu Leu Phe Glu Glu Ala
    1055              1060              1065

Phe Ala Ile Phe Arg Lys Phe Asp Val Asn Thr Ser Ala Val Gln
    1070              1075              1080
```

```
Val Leu Ile Glu His Ile Gly Asn Leu Asp Arg Ala Tyr Glu Phe
    1085            1090                1095

Ala Glu Arg Cys Asn Glu Pro Ala Val Trp Ser Gln Leu Ala Lys
    1100            1105                1110

Ala Gln Leu Gln Lys Gly Met Val Lys Glu Ala Ile Asp Ser Tyr
    1115            1120                1125

Ile Lys Ala Asp Asp Pro Ser Ser Tyr Met Glu Val Val Gln Ala
    1130            1135                1140

Ala Asn Thr Ser Gly Asn Trp Glu Glu Leu Val Lys Tyr Leu Gln
    1145            1150                1155

Met Ala Arg Lys Lys Ala Arg Glu Ser Tyr Val Glu Thr Glu Leu
    1160            1165                1170

Ile Phe Ala Leu Ala Lys Thr Asn Arg Leu Ala Glu Leu Glu Glu
    1175            1180                1185

Phe Ile Asn Gly Pro Asn Asn Ala His Ile Gln Gln Val Gly Asp
    1190            1195                1200

Arg Cys Tyr Asp Glu Lys Met Tyr Asp Ala Ala Lys Leu Leu Tyr
    1205            1210                1215

Asn Asn Val Ser Asn Phe Gly Arg Leu Ala Ser Thr Leu Val His
    1220            1225                1230

Leu Gly Glu Tyr Gln Ala Ala Val Asp Gly Ala Arg Lys Ala Asn
    1235            1240                1245

Ser Thr Arg Thr Trp Lys Glu Val Cys Phe Ala Cys Val Asp Gly
    1250            1255                1260

Lys Glu Phe Arg Leu Ala Gln Met Cys Gly Leu His Ile Val Val
    1265            1270                1275

His Ala Asp Glu Leu Glu Glu Leu Ile Asn Tyr Tyr Gln Asp Arg
    1280            1285                1290

Gly Tyr Phe Glu Glu Leu Ile Thr Met Leu Glu Ala Ala Leu Gly
    1295            1300                1305

Leu Glu Arg Ala His Met Gly Met Phe Thr Glu Leu Ala Ile Leu
    1310            1315                1320

Tyr Ser Lys Phe Lys Pro Gln Lys Met Arg Glu His Leu Glu Leu
    1325            1330                1335

Phe Trp Ser Arg Val Asn Ile Pro Lys Val Leu Arg Ala Ala Glu
    1340            1345                1350

Gln Ala His Leu Trp Ala Glu Leu Val Phe Leu Tyr Asp Lys Tyr
    1355            1360                1365

Glu Glu Tyr Asp Asn Ala Ile Ile Thr Met Met Asn His Pro Thr
    1370            1375                1380

Asp Ala Trp Lys Glu Gly Gln Phe Lys Asp Ile Ile Thr Lys Val
    1385            1390                1395

Ala Asn Val Glu Leu Tyr Tyr Arg Ala Ile Gln Phe Tyr Leu Glu
    1400            1405                1410

Phe Lys Pro Leu Leu Leu Asn Asp Leu Leu Met Val Leu Ser Pro
    1415            1420                1425

Arg Leu Asp His Thr Arg Ala Val Asn Tyr Phe Ser Lys Val Lys
    1430            1435                1440

Gln Leu Pro Leu Val Lys Pro Tyr Leu Arg Ser Val Gln Asn His
    1445            1450                1455

Asn Asn Lys Ser Val Asn Glu Ser Leu Asn Leu Phe Ile Thr Glu
    1460            1465                1470
```

| | | | | | | | | | | | |
|---|---|---|---|---|---|---|---|---|---|---|---|
| Glu | Asp | Tyr | Gln | Ala | Leu | Arg | Thr | Ser | Ile | Asp | Ala | Tyr | Asp | Asn |
| 1475 | | | | | 1480 | | | | | 1485 | | | | |

Phe Asp Asn Ile Ser Leu Ala Gln Arg Leu Glu Lys His Glu Leu
1490                     1495                    1500

Ile Glu Phe Arg Arg Ile Ala Ala Tyr Leu Phe Lys Gly Asn Asn
1505                     1510                    1515

Arg Trp Lys Gln Ser Val Glu Leu Cys Lys Lys Asp Ser Leu Tyr
1520                     1525                    1530

Lys Asp Ala Met Gln Tyr Ala Ser Glu Ser Lys Asp Thr Glu Leu
1535                     1540                    1545

Ala Glu Glu Leu Leu Gln Trp Phe Leu Gln Glu Lys Arg Glu
1550                     1555                    1560

Cys Phe Gly Ala Cys Leu Phe Thr Cys Tyr Asp Leu Leu Arg Pro
1565                     1570                    1575

Asp Val Val Leu Glu Thr Ala Trp Arg His Asn Ile Met Asp Phe
1580                     1585                    1590

Ala Met Pro Tyr Phe Ile Gln Val Met Lys Glu Tyr Leu Thr Lys
1595                     1600                    1605

Val Asp Lys Leu Asp Ala Ser Glu Ser Leu Arg Lys Glu Glu Glu
1610                     1615                    1620

Gln Ala Thr Glu Thr Gln Pro Ile Val Tyr Gly Asn Leu Ser Leu
1625                     1630                    1635

<210> SEQ ID NO 2
<211> LENGTH: 4917
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atggcgcaga tcctgccgat tcgcttccag gaacacctgc aactgcaaaa cctgggcatc      60
aacccggcaa acatcggttt ctctaccctg actatggagt ctgataagtt tatctgtatc     120
cgtgagaaag tgggtgagca ggctcaggtg gtgattattg acatgaacga cccgtctaac     180
ccgatccgtc gcccgatctc cgcagattcc gcaatcatga cccggcgtc caaggttatc     240 gcgctgaaag ctggtaagac cctgcaaatc tttaacattg agatgaagtc caaaatgaag     300
gcgcatacca tgaccgacga cgttaccttc tggaagtgga tctctctgaa caccgttgca     360
ctggttactg acaacgcggt gtaccactgg tctatggaag gtaatcca gccggttaaa     420 atgttcgacc gtcattcttc tctggcgggt tgccagatta tcaactaccg taccgacgcg     480
aaacagaaat ggctgctgct gactggcatt tccgcacagc agaaccgcgt ggttggtgca     540
atgcagctgt actctgtgga ccgtaaggtg tctcagccga tcgaaggtca cgctgcgtcc     600
tttgcgcagt tcaagatgga gggtaacgcg aagaatcca ccctgttttg ctttgcggtg     660
cgtggccagg cgggtggtaa actgcatatt atcgaggttg cgactccgcc gaccggcaac     720
cagccgttcc cgaaaaaagc ggttgacgtt ttctttccgc cggaagctca gaacgacttc     780
ccggttgcga tgcagattag cgagaaacac gacgtggttt tcctgattac caagtacggc     840
tacatccacc tgtacgacct ggagactggc acctgcatct atatgaaccg tatctctggt     900
gaaaccatct tcgttactgc tccgcatgag gcgaccgctg gtatcatcgg tgttaaccgt     960
aaaggtcagg tgctgtctgt ttgtgttgag aagagaaca tcatcccgta catcactaac    1020
gttctgcaaa acccggacct ggcgctgcgc atggcggttc gcaacaacct ggcaggcgct    1080
```

```
gaggagctgt tcgcgcgtaa attcaacgcg ctgtttgctc agggcaacta ttctgaagcg   1140
gcgaaagttg ctgcaaacgc gccgaaaggc atcctgcgta ctccggacac catccgccgt   1200
ttccagtccg tgccggcgca gccgggtcag acctccccgc tgctgcaata ttttggtatc   1260
ctgctggacc agggtcagct gaacaagtat gaaagcctgg aactgtgccg tccggtgctg   1320
caacagggcc gtaaacagct gctggagaag tggctgaagg aagacaaact ggaatgctcc   1380
gaagagctgg gtgacctggt taaatccgtg acccgactc tggcactgag cgtgtatctg   1440
cgtgcgaacg tgccgaacaa agttatccag tgcttcgcgg aaaccggcca ggtgcagaag   1500
attgttctgt acgcaaaaaa agttggctat accccggatt ggatcttct gctgcgtaac   1560 gtgatgcgta tcagcccgga tcagggccag cagtttgcac agatgctggt tcaggacgag   1620
gagccgctgg cggacattac ccagatcgtt gatgttttta tggaatataa cctgattcag   1680
cagtgtactg cgttcctgct ggatgctctg aaaaacaacc gtccgtctga gggtccgctg   1740
caaactcgtc tgctggaaat gaacctgatg cacgcgccgc aggtggcaga tgcaattctg   1800
ggcaaccaga tgttcactca ctatgaccgc gctcatatcg cgcagctgtg cgaaaaagcg   1860
ggtctgctgc aacgtgcgct ggagcatttc accgacctgt acgacattaa gcgtgctgtg   1920
gtgcatactc atctgctgaa cccggaatgg ctggttaact atttcggttc tctgagcgtg   1980
gaagactccc tggagtgcct gcgcgcgatg ctgtccgcaa acatccgtca gaacctgcaa   2040
atttgtgttc aggtggcttc taaataccat gaacagctga gcacccagtc tctgattgag   2100
ctgtttgaat ctttcaagtc cttcgagggc ctgttctact tcctgggttc tatcgtgaac   2160
ttctctcagg acccggacgt tcatttcaaa tacattcagg ctgcgtgcaa aactggtcag   2220
atcaaagaag tggaacgtat ctgccgcgaa tctaactgct acgacccgga gcgcgtgaag   2280
aactttctga agaagcgaa gctgaccgac cagctgccgc tgatcatcgt tgtgaccgt   2340 ttcgacttcg ttcatgatct ggtgctgtac ctgtatcgta caacctgca aaagtacatt   2400 gagatttacg ttcagaaggt gaacccgtct cgtctgccgg tggttattgg tggcctgctg   2460
gatgtggact gctctgaaga cgttatcaaa aacctgatcc tggttgttcg tggccagttc   2520
tccaccgatg aactggtggc tgaggttgaa aagcgtaacc gtctgaaact gctgctgccg   2580
tggctggaag cgcgtatcca cgaaggttgt gaggaaccgg cgacccataa cgcgctggcg   2640
aaaatctata tcgactctaa caacaacccg gaacgcttcc tgcgtgaaaa cccgtattac   2700
gactctcgtg ttgtgggtaa atactgtgag aaacgtgatc cgcacctggc gtgtgttgcg   2760
tacgaacgtg gtcagtgcga cctggaactg atcaacgttt gtaacgaaaa ctctctgttc   2820
aaatctctgt ctcgttacct ggtgcgtcgc aaagatccgg agctgtgggg tagcgttctg   2880
ctggaatcca cccgtaccg tcgtccgctg attgaccagg tggttcagac tgcgctgagc   2940
gagactcagg acccggagga agttagcgtt accgttaaag cattcatgac tgcggacctg   3000
ccgaacgagc tgatcgagct gctggagaaa attgttctgg acaactccgt ttttagcgaa   3060
caccgcaacc tgcaaaacct gctgattctg actgcgatca aggcggatcg tacccgcgtg   3120
atggaatata tcaaccgcct ggataactat gatgcgccgg acatcgcgaa catcgctatc   3180
tctaacgaac tgttcgaaga agcgtttgcg attttccgta aattcgacgt taacacctct   3240
gcggtgcagg tgctgatcga acatatcggt aacctggacc gtgcgtatga gttcgcagag   3300
cgctgcaacg agccggcagt ttggtcccag ctggcaaagg ctcagctgca aagggtatg   3360 gttaaagaag caatcgactc ttacatcaaa gcggatgatc cgtctagcta tatggaagtt   3420
```

| | | |
|---|---|---|
| gtgcaggcag cgaacacctc cggtaactgg gaggagctgg tgaagtacct gcaaatggcg | 3480 | |
| cgcaaaaagg cgcgtgaatc ttatgtggag accgagctga ttttcgcgct ggcgaaaacc | 3540 | |
| aaccgcctgg cggaactgga ggagtttatc aacggtccga caacgctca tatccagcag | 3600 | |
| gttggcgatc gttgctacga cgaaaaaatg tacgacgcgg cgaagctgct gtacaacaac | 3660 | |
| gtttctaact tcggccgtct ggcttctact ctggtgcatc tgggcgagta tcaggctgcg | 3720 | |
| gtggacggtg cgcgtaaagc gaactctacc cgcacttgga agaagtttg cttcgcgtgt | 3780 | |
| gttgacggca agaatttcg tctggcgcag atgtgcggtc tgcacattgt ggtgcacgct | 3840 | |
| gacgagctgg aagagctgat caactactat caggatcgtg ttactttga agaactgatc | 3900 | |
| accatgctgg aggcggcact gggtctggaa cgtgctcaca tgggtatgtt caccgaactg | 3960 | |
| gcaatcctgt actctaaatt caagccgcag aaaatgcgcg agcacctgga actgttttgg | 4020 | |
| agccgcgtta acatcccgaa ggttctgcgt gcggcggagc aggcgcatct gtgggctgaa | 4080 | |
| ctggtgtttc tgtatgataa gtatgaggaa tatgacaacg cgattatcac tatgatgaac | 4140 | |
| catccgaccg acgcgtggaa ggaaggtcag tttaaggaca tcatcactaa agtggcgaac | 4200 | |
| gtggagctgt actaccgtgc gatccagttt tacctggagt tcaaaccgct gctgctgaac | 4260 | |
| gatctgctga tggtgctgtc tccgcgtctg gaccacaccc gtgctgtgaa ctacttctct | 4320 | |
| aaggttaaac agctgccgct ggttaagccg tatctgcgta gcgttcagaa ccataacaac | 4380 | |
| aagagcgtga acgaatccct gaacaacctg ttcattaccg aagaagacta ccaggcactg | 4440 | |
| cgtacctcta tcgatgctta cgacaacttt gataacatct ctctggcaca gcgcctggaa | 4500 | |
| aaacatgaac tgattgagtt ccgtcgcatc gcggcttatc tgttcaaggg caacaaccgt | 4560 | |
| tggaaacagt ctgttgagct gtgcaaaaaa gattctctgt ataaagatgc aatgcagtac | 4620 | |
| gcgtccgaat ctaaagacac tgagctggct gaggaactgc tgcaatggtt cctgcaagag | 4680 | |
| gagaagcgcg agtgcttcgg tgcttgcctg tttacttgct atgacctgct gcgtccggat | 4740 | |
| gttgttctgg aaactgcttg gcgtcataac attatggact ttgcgatgcc gtactttatc | 4800 | |
| caggttatga agaatatct gaccaaagtg gacaagctgg acgcgagcga aagcctgcgc | 4860 | |
| aaggaggaag aacaggctac cgaaacccag ccgatcgtgt acggtaacct gtctctg | 4917 | |

<210> SEQ ID NO 3
<211> LENGTH: 1647
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 3

Met Ala Gln Ile Leu Pro Ile Arg Phe Gln Glu His Leu Gln Leu Gln
1               5                   10                  15

Asn Leu Gly Ile Asn Pro Ala Asn Ile Gly Phe Ser Thr Leu Thr Met
            20                  25                  30

Glu Ser Asp Lys Phe Ile Cys Ile Arg Glu Lys Val Gly Glu Gln Ala
        35                  40                  45

Gln Val Val Ile Ile Asp Met Asn Asp Pro Ser Asn Pro Ile Arg Arg
    50                  55                  60

Pro Ile Ser Ala Asp Ser Ala Ile Met Asn Pro Ala Ser Lys Val Ile
65                  70                  75                  80

Phe Asn Ile Glu Met Lys Ser Lys Met Lys Ala His Thr Met Thr Asp
                85                  90                  95

```
Asp Val Thr Phe Trp Lys Trp Ile Ser Leu Asn Thr Val Ala Leu Val
            100                 105                 110
Thr Asp Asn Ala Val Tyr His Trp Ser Met Glu Gly Glu Ser Gln Pro
        115                 120                 125
Val Lys Met Phe Asp Arg His Ser Ser Leu Ala Gly Cys Gln Ile Ile
    130                 135                 140
Asn Tyr Arg Thr Asp Ala Ala Leu Lys Ala Gly Lys Thr Leu Gln Ile
145                 150                 155                 160
Lys Gln Lys Trp Leu Leu Thr Gly Ile Ser Ala Gln Gln Asn Arg
                165                 170                 175
Val Val Gly Ala Met Gln Leu Tyr Ser Val Asp Arg Lys Val Ser Gln
            180                 185                 190
Pro Ile Glu Gly His Ala Ala Ser Phe Ala Gln Phe Lys Met Glu Gly
        195                 200                 205
Asn Ala Glu Glu Ser Thr Leu Phe Cys Phe Ala Val Arg Gly Gln Ala
    210                 215                 220
Gly Gly Lys Leu His Ile Ile Glu Val Gly Thr Pro Thr Gly Asn
225                 230                 235                 240
Gln Pro Phe Pro Lys Lys Ala Val Asp Val Phe Phe Pro Glu Ala
                245                 250                 255
Gln Asn Asp Phe Pro Val Ala Met Gln Ile Ser Glu Lys His Asp Val
            260                 265                 270
Val Phe Leu Ile Thr Lys Tyr Gly Tyr Ile His Leu Tyr Asp Leu Glu
        275                 280                 285
Thr Gly Thr Cys Ile Tyr Met Asn Arg Ile Ser Gly Glu Thr Ile Phe
    290                 295                 300
Val Thr Ala Pro His Glu Ala Thr Ala Gly Ile Ile Gly Val Asn Arg
305                 310                 315                 320
Lys Gly Gln Val Leu Ser Val Cys Val Glu Glu Asn Ile Ile Pro
                325                 330                 335
Tyr Ile Thr Asn Val Leu Gln Asn Pro Asp Leu Ala Leu Arg Met Ala
            340                 345                 350
Val Arg Asn Asn Leu Ala Gly Ala Glu Glu Leu Phe Ala Arg Lys Phe
        355                 360                 365
Asn Ala Leu Phe Ala Gln Gly Asn Tyr Ser Glu Ala Ala Lys Val Ala
    370                 375                 380
Ala Asn Ala Pro Lys Gly Ile Leu Arg Thr Pro Asp Thr Ile Arg Arg
385                 390                 395                 400
Phe Gln Ser Val Pro Ala Gln Pro Gly Gln Thr Ser Pro Leu Leu Gln
                405                 410                 415
Tyr Phe Gly Ile Leu Leu Asp Gln Gly Gln Leu Asn Lys Tyr Glu Ser
            420                 425                 430
Leu Glu Leu Cys Arg Pro Val Leu Gln Gln Gly Arg Lys Gln Leu Leu
        435                 440                 445
Glu Lys Trp Leu Lys Glu Asp Lys Leu Glu Cys Ser Glu Glu Leu Gly
    450                 455                 460
Asp Leu Val Lys Ser Val Asp Pro Thr Leu Ala Leu Ser Val Tyr Leu
465                 470                 475                 480
Arg Ala Asn Val Pro Asn Lys Val Ile Gln Cys Phe Ala Glu Thr Gly
                485                 490                 495
Gln Val Gln Lys Ile Val Leu Tyr Ala Lys Lys Val Gly Tyr Thr Pro
            500                 505                 510
Asp Trp Ile Phe Leu Leu Arg Asn Val Met Arg Ile Ser Pro Asp Gln
```

-continued

```
                515                 520                 525
Gly Gln Gln Phe Ala Gln Met Leu Val Gln Asp Glu Pro Leu Ala
        530                 535                 540
Asp Ile Thr Gln Ile Val Asp Val Phe Met Glu Tyr Asn Leu Ile Gln
545                 550                 555                 560
Gln Cys Thr Ala Phe Leu Leu Asp Ala Leu Lys Asn Asn Arg Pro Ser
                565                 570                 575
Glu Gly Pro Leu Gln Thr Arg Leu Leu Glu Met Asn Leu Met His Ala
            580                 585                 590
Pro Gln Val Ala Asp Ala Ile Leu Gly Asn Gln Met Phe Thr His Tyr
            595                 600                 605
Asp Arg Ala His Ile Ala Gln Leu Cys Glu Lys Ala Gly Leu Leu Gln
610                 615                 620
Arg Ala Leu Glu His Phe Thr Asp Leu Tyr Asp Ile Lys Arg Ala Val
625                 630                 635                 640
Val His Thr His Leu Leu Asn Pro Glu Trp Leu Val Asn Tyr Phe Gly
            645                 650                 655
Ser Leu Ser Val Glu Asp Ser Leu Glu Cys Leu Arg Ala Met Leu Ser
            660                 665                 670
Ala Asn Ile Arg Gln Asn Leu Gln Ile Cys Val Gln Val Ala Ser Lys
            675                 680                 685
Tyr His Glu Gln Leu Ser Thr Gln Ser Leu Ile Glu Leu Phe Glu Ser
    690                 695                 700
Phe Lys Ser Phe Glu Gly Leu Phe Tyr Phe Leu Gly Ser Ile Val Asn
705                 710                 715                 720
Phe Ser Gln Asp Pro Asp Val His Phe Lys Tyr Ile Gln Ala Ala Cys
                725                 730                 735
Lys Thr Gly Gln Ile Lys Glu Val Glu Arg Ile Cys Arg Glu Ser Asn
            740                 745                 750
Cys Tyr Asp Pro Glu Arg Val Lys Asn Phe Leu Lys Glu Ala Lys Leu
        755                 760                 765
Thr Asp Gln Leu Pro Leu Ile Ile Val Cys Asp Arg Phe Asp Phe Val
    770                 775                 780
His Asp Leu Val Leu Tyr Leu Tyr Arg Asn Asn Leu Gln Lys Tyr Ile
785                 790                 795                 800
Glu Ile Tyr Val Gln Lys Val Asn Pro Ser Arg Leu Pro Val Val Ile
                805                 810                 815
Gly Gly Leu Leu Asp Val Asp Cys Ser Glu Asp Val Ile Lys Asn Leu
            820                 825                 830
Ile Leu Val Val Arg Gly Gln Phe Ser Thr Asp Glu Leu Val Ala Glu
        835                 840                 845
Val Glu Lys Arg Asn Arg Leu Lys Leu Leu Leu Pro Trp Leu Glu Ala
    850                 855                 860
Arg Ile His Glu Gly Cys Glu Glu Pro Ala Thr His Asn Ala Leu Ala
865                 870                 875                 880
Lys Ile Tyr Ile Asp Ser Asn Asn Pro Glu Arg Phe Leu Arg Glu
                885                 890                 895
Asn Pro Tyr Tyr Asp Ser Arg Val Val Gly Lys Tyr Cys Glu Lys Arg
            900                 905                 910
Asp Pro His Leu Ala Cys Val Ala Tyr Glu Arg Gly Gln Cys Asp Leu
        915                 920                 925
Glu Leu Ile Asn Val Cys Asn Glu Asn Ser Leu Phe Lys Ser Leu Ser
    930                 935                 940
```

```
Arg Tyr Leu Val Arg Arg Lys Asp Pro Glu Leu Trp Gly Ser Val Leu
945                 950                 955                 960

Leu Glu Ser Asn Pro Tyr Arg Arg Pro Leu Ile Asp Gln Val Val Gln
                965                 970                 975

Thr Ala Leu Ser Glu Thr Gln Asp Pro Glu Glu Val Ser Val Thr Val
            980                 985                 990

Lys Ala Phe Met Thr Ala Asp Leu Pro Asn Glu Leu Ile Glu Leu Leu
        995                 1000                1005

Glu Lys Ile Val Leu Asp Asn Ser Val Phe Ser Glu His Arg Asn
    1010                1015                1020

Leu Gln Asn Leu Leu Ile Leu Thr Ala Ile Lys Ala Asp Arg Thr
    1025                1030                1035

Arg Val Met Glu Tyr Ile Asn Arg Leu Asp Asn Tyr Asp Ala Pro
    1040                1045                1050

Asp Ile Ala Asn Ile Ala Ile Ser Asn Glu Leu Phe Glu Glu Ala
    1055                1060                1065

Phe Ala Ile Phe Arg Lys Phe Asp Val Asn Thr Ser Ala Val Gln
    1070                1075                1080

Val Leu Ile Glu His Ile Gly Asn Leu Asp Arg Ala Tyr Glu Phe
    1085                1090                1095

Ala Glu Arg Cys Asn Glu Pro Ala Val Trp Ser Gln Leu Ala Lys
    1100                1105                1110

Ala Gln Leu Gln Lys Gly Met Val Lys Glu Ala Ile Asp Ser Tyr
    1115                1120                1125

Ile Lys Ala Asp Asp Pro Ser Ser Tyr Met Glu Val Val Gln Ala
    1130                1135                1140

Ala Asn Thr Ser Gly Asn Trp Glu Glu Leu Val Lys Tyr Leu Gln
    1145                1150                1155

Met Ala Arg Lys Lys Ala Arg Glu Ser Tyr Val Glu Thr Glu Leu
    1160                1165                1170

Ile Phe Ala Leu Ala Lys Thr Asn Arg Leu Ala Glu Leu Glu Glu
    1175                1180                1185

Phe Ile Asn Gly Pro Asn Asn Ala His Ile Gln Gln Val Gly Asp
    1190                1195                1200

Arg Cys Tyr Asp Glu Lys Met Tyr Asp Ala Ala Lys Leu Leu Tyr
    1205                1210                1215

Asn Asn Val Ser Asn Phe Gly Arg Leu Ala Ser Thr Leu Val His
    1220                1225                1230

Leu Gly Glu Tyr Gln Ala Ala Val Asp Gly Ala Arg Lys Ala Asn
    1235                1240                1245

Ser Thr Arg Thr Trp Lys Glu Val Cys Phe Ala Cys Val Asp Gly
    1250                1255                1260

Lys Glu Phe Arg Leu Ala Gln Met Cys Gly Leu His Ile Val Val
    1265                1270                1275

His Ala Asp Glu Leu Glu Glu Leu Ile Asn Tyr Tyr Gln Asp Arg
    1280                1285                1290

Gly Tyr Phe Glu Glu Leu Ile Thr Met Leu Glu Ala Ala Leu Gly
    1295                1300                1305

Leu Glu Arg Ala His Met Gly Met Phe Thr Glu Leu Ala Ile Leu
    1310                1315                1320

Tyr Ser Lys Phe Lys Pro Gln Lys Met Arg Glu His Leu Glu Leu
    1325                1330                1335
```

```
Phe Trp Ser Arg Val Asn Ile Pro Lys Val Leu Arg Ala Ala Glu
    1340            1345                1350
Gln Ala His Leu Trp Ala Glu Leu Val Phe Leu Tyr Asp Lys Tyr
    1355            1360                1365
Glu Glu Tyr Asp Asn Ala Ile Ile Thr Met Met Asn His Pro Thr
    1370            1375                1380
Asp Ala Trp Lys Glu Gly Gln Phe Lys Asp Ile Ile Thr Lys Val
    1385            1390                1395
Ala Asn Val Glu Leu Tyr Tyr Arg Ala Ile Gln Phe Tyr Leu Glu
    1400            1405                1410
Phe Lys Pro Leu Leu Leu Asn Asp Leu Leu Met Val Leu Ser Pro
    1415            1420                1425
Arg Leu Asp His Thr Arg Ala Val Asn Tyr Phe Ser Lys Val Lys
    1430            1435                1440
Gln Leu Pro Leu Val Lys Pro Tyr Leu Arg Ser Val Gln Asn His
    1445            1450                1455
Asn Asn Lys Ser Val Asn Glu Ser Leu Asn Asn Leu Phe Ile Thr
    1460            1465                1470
Glu Glu Asp Tyr Gln Ala Leu Arg Thr Ser Ile Asp Ala Tyr Asp
    1475            1480                1485
Asn Phe Asp Asn Ile Ser Leu Ala Gln Arg Leu Glu Lys His Glu
    1490            1495                1500
Leu Ile Glu Phe Arg Arg Ile Ala Ala Tyr Leu Phe Lys Gly Asn
    1505            1510                1515
Asn Arg Trp Lys Gln Ser Val Glu Leu Cys Lys Lys Asp Ser Leu
    1520            1525                1530
Tyr Lys Asp Ala Met Gln Tyr Ala Ser Glu Ser Lys Asp Thr Glu
    1535            1540                1545
Leu Ala Glu Glu Leu Leu Gln Trp Phe Leu Gln Glu Glu Lys Arg
    1550            1555                1560
Glu Cys Phe Gly Ala Cys Leu Phe Thr Cys Tyr Asp Leu Leu Arg
    1565            1570                1575
Pro Asp Val Val Leu Glu Thr Ala Trp Arg His Asn Ile Met Asp
    1580            1585                1590
Phe Ala Met Pro Tyr Phe Ile Gln Val Met Lys Glu Tyr Leu Thr
    1595            1600                1605
Lys Val Asp Lys Leu Asp Ala Ser Glu Ser Leu Arg Lys Glu Glu
    1610            1615                1620
Glu Gln Ala Thr Glu Thr Gln Pro Ile Val Tyr Gly Asn Leu Ser
    1625            1630                1635
Leu Leu Glu His His His His His His
    1640            1645

<210> SEQ ID NO 4
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Glu Leu Asp Pro Phe Gly Ala Pro Ala Gly Ala Pro Gly Gly
1               5                   10                  15
Pro Ala Leu Gly Asn Gly Val Ala Gly Ala Gly Glu Glu Asp Pro Ala
            20                  25                  30
```

Ala Ala Phe Leu Ala Gln Gln Glu Ser Glu Ile Ala Gly Ile Glu Asn
         35                  40                  45

Asp Glu Ala Phe Ala Ile Leu Asp Gly Gly Ala Pro Gly Pro Gln Pro
 50                  55                  60

His Gly Glu Pro Pro Gly Gly Pro Asp Ala Val Asp Gly Val Met Asn
 65                  70                  75                  80

Gly Glu Tyr Tyr Gln Glu Ser Asn Gly Pro Thr Asp Ser Tyr Ala Ala
                 85                  90                  95

Ile Ser Gln Val Asp Arg Leu Gln Ser Glu Pro Ser Ile Arg Lys
                100                 105                 110

Trp Arg Glu Glu Gln Met Glu Arg Leu Glu Ala Leu Asp Ala Asn Ser
                115                 120                 125

Arg Lys Gln Glu Ala Glu Trp Lys Glu Lys Ala Ile Lys Glu Leu Glu
130                 135                 140

Glu Trp Tyr Ala Arg Gln Asp Glu Gln Leu Gln Lys Thr Lys Ala Asn
145                 150                 155                 160

Asn Arg Val Ala Asp Glu Ala Phe Tyr Lys Gln Pro Phe Ala Asp Val
                165                 170                 175

Ile Gly Tyr Val Thr Asn Ile Asn His Pro Cys Tyr Ser Leu Glu Gln
                180                 185                 190

Ala Ala Glu Glu Ala Phe Val Asn Asp Ile Asp Glu Ser Ser Pro Gly
                195                 200                 205

Thr Glu Trp Glu Arg Val Ala Arg Leu Cys Asp Phe Asn Pro Lys Ser
210                 215                 220

Ser Lys Gln Ala Lys Asp Val Ser Arg Met Arg Ser Val Leu Ile Ser
225                 230                 235                 240

Leu Lys Gln Ala Pro Leu Val His
                245

<210> SEQ ID NO 5
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atggcggaac tggacccgtt cggcgctccg gcaggcgcac cgggcggtcc ggcgctgggt      60
aacggcgttg cgggtgctgg tgaagaagac ccggcagcag cgttcctggc cagcaggaa     120 tctgaaatcg caggtatcga aacgatgaa gcgttcgcga tcctggacgg tggtgctccg     180
ggtccgcagc cgcacggtga accgccgggt ggtccggatg cggttgacgg tgttatgaac    240
ggcgagtact accaggagtc taacggtccg accgattctt acgcggcaat tagccaggtt    300
gatcgtctgc aatccgaacc ggaatctatc cgtaaatggc gtgaggagca gatggaacgc    360
ctggaagctc tggacgcgaa ctctcgcaaa caggaggcga atggaaaga aaaagcgatc     420 aaagagctgg aagaatggta tgcgcgtcag gacgaacagc tgcaaaaaac caaagcgaac    480
aaccgtgtgg cggacgaagc attctacaaa cagccgtttg cggacgttat cggttacgtt    540
accaacatca accatccgtg ctactctctg gagcaggcag cggaagaagc gttcgtgaac    600
gacatcgacg aatctagccc aggcaccgaa tgggaacgtg ttgcgcgcct gtgcgacttc    660
aacccgaaat cttctaaaca ggctaaagac gtttctcgta tgcgttctgt tctgatctct    720
ctgaagcagg ctccgctggt tcac                                           744

<210> SEQ ID NO 6
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Glu Leu Asp Pro Phe Gly Ala Pro Ala Gly Ala Pro Gly Gly
1               5                   10                  15

Pro Ala Leu Gly Asn Gly Val Ala Gly Ala Gly Glu Glu Asp Pro Ala
            20                  25                  30

Ala Ala Phe Leu Ala Gln Gln Glu Ser Glu Ile Ala Gly Ile Glu Asn
        35                  40                  45

Asp Glu Ala Phe Ala Ile Leu Asp Gly Gly Ala Pro Gly Pro Gln Pro
    50                  55                  60

His Gly Glu Pro Pro Gly Gly Pro Asp Ala Val Asp Gly Val Met Asn
65                  70                  75                  80

Gly Glu Tyr Tyr Gln Glu Ser Asn Gly Pro Thr Asp Ser Tyr Ala Ala
                85                  90                  95

Ile Ser Gln Val Asp Arg Leu Gln Ser Glu Pro Glu Ser Ile Arg Lys
            100                 105                 110

Trp Arg Glu Glu Gln Met Glu Arg Leu Glu Ala Leu Asp Ala Asn Ser
        115                 120                 125

Arg Lys Gln Glu Ala Glu Trp Lys Glu Lys Ala Ile Lys Glu Leu Glu
    130                 135                 140

Glu Trp Tyr Ala Arg Gln Asp Glu Gln Leu Gln Lys Thr Lys Ala Asn
145                 150                 155                 160

Asn Arg Val Ala Asp Glu Ala Phe Tyr Lys Gln Pro Phe Ala Asp Val
                165                 170                 175

Ile Gly Tyr Val Thr Asn Ile Asn His Pro Cys Tyr Ser Leu Glu Gln
            180                 185                 190

Ala Ala Glu Glu Ala Phe Val Asn Asp Ile Asp Glu Ser Ser Pro Gly
        195                 200                 205

Thr Glu Trp Glu Arg Val Ala Arg Leu Cys Asp Phe Asn Pro Lys Ser
    210                 215                 220

Ser Lys Gln Ala Lys Asp Val Ser Arg Met Arg Ser Val Leu Ile Ser
225                 230                 235                 240

Leu Lys Gln Ala Pro Leu Val His Leu Glu His His His His His
                245                 250                 255

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5

<210> SEQ ID NO 8
<211> LENGTH: 23
<212> TYPE: DNA
<213> ORGANISM: Artificial Sequence -continued

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(21)
<223> OTHER INFORMATION: a, c, t, g, unknown or other

<400> SEQUENCE: 8
aannnnnnnn nnnnnnnnnn ntt                                              23

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Asp Cys Arg Gly Asp Cys Phe Cys
1               5
```

SELF ASSEMBLING MOLECULES FOR TARGETED DRUG DELIVERY

RELATED APPLICATIONS

This application is a continuation of U.S. application Ser. No. 15/563,339, filed Sep. 29, 2017, which is the United States National Stage application of PCT/US16/025290, filed Mar. 31, 2016, which claims the benefit of priority to U.S. Provisional Patent Application Ser. No. 62/140,696, filed Mar. 31, 2015, the contents of each of which are hereby incorporated by reference.

SEQUENCE LISTING

The instant application contains a Sequence Listing which has been submitted electronically in ASCII format and is hereby incorporated by reference in its entirety. Said ASCII copy, created on Oct. 17, 2017, is named MAA-02301_SL.txt and is 42,181 bytes in size.

BACKGROUND

Many extremely useful chemotherapeutics lose their potential utility as effective cancer therapy due to their systemic toxicity. As a result, drug delivery systems have been a significant focus of research in the anti-cancer arena. For example, large particulate assemblies of biologically compatible materials, such as liposomes, have been used as carriers for administration of drugs and paramagnetic contrast agents. For example, liposome compositions containing an entrapped agent, such as a drug, are known; these compositions are engineered to control biodistribution and recirculatory half-life.

In order to provide a therapeutic effect, a sufficient concentration of an active agent must be delivered to a targeted site. So, there is a need for recirculation of the active agent in the body. Active agents and delivery systems that avoid rapid endocytosis by the reticuloendothelial (RE) system or rapid filtration by the kidney are desirable. Experience with magnetic resonance contrast agents has provided useful information regarding circulation lifetimes. Small molecules, such as gadolinium diethylenetriaminepentaacetic acid, tend to have limited circulation times due to rapid renal excretion while most liposomes, having diameters greater than 800 nm, are quickly cleared by the reticuloendothelial system. Attempts to solve these problems have involved use of macromolecular materials, such as gadolinium diethylenetriaminepentaacetic acid-derived polysaccharides, polypeptides, and proteins. These agents have not achieved the versatility in chemical modification to provide for both long recirculation times and active targeting. In addition, the use of targeted antibodies, immune-enhancing drugs, slow-release peptides, or polymers for targeted drug delivery results in extreme side-effects or low delivery efficiency (e.g, the delivery systems are not internalized by the cells).

Accordingly, there is a need for improved anti-cancer therapeutics and delivery systems.

SUMMARY

In certain embodiments, the invention relates to a first composition comprising a protein, a first payload, and a first targeting agent, wherein the protein is in the form of a three-dimensional cage structure comprising an outer surface and an inner cavity; and the first targeting agent is conjugated to the outer surface of the three-dimensional cage structure.

In certain embodiments, the invention relates to any of the first compositions described herein, wherein the first payload is an anti-cancer agent.

In certain embodiments, the invention relates to any of the first compositions described herein, wherein the first payload is an imaging agent.

In certain embodiments, the invention relates to any of the first compositions described herein, wherein the first targeting agent selectively targets cancer cells as compared to healthy cells.

In certain embodiments, the invention relates to any of the first compositions described herein, wherein the first targeting agent specifically targets cancer cells.

In certain embodiments, the invention relates to any of the first compositions described herein, wherein the first targeting agent is an antibody.

In certain embodiments, the invention relates to any of the first compositions described herein, wherein the protein is clathrin or a clathrin derivative.

In certain embodiments, the invention relates to any of the first compositions described herein, wherein the first composition or the second composition is able to transfect cells in vivo.

In certain embodiments, the invention relates to a second composition comprising a protein, a second payload, and a second targeting agent, wherein the protein is in the form of a three-dimensional cage structure comprising an outer surface and an inner cavity; the second payload is an immunogen; and the second targeting agent conjugated to the outer surface of the three-dimensional cage structure.

In certain embodiments, the invention relates to any of the second compositions described herein, wherein the second targeting agent does not selectively target cancer cells as compared to healthy cells.

In certain embodiments, the invention relates to any of the second compositions described herein, wherein the second targeting agent is an antibody.

In certain embodiments, the invention relates to any of the second compositions described herein, wherein the second targeting agent is an anti-PD-1 antibody.

In certain embodiments, the invention relates to any of the second compositions described herein, wherein the protein is clathrin or a clathrin derivative.

In certain embodiments, the invention relates to any of the second compositions described herein, wherein the second composition is able to transfect cells in vivo.

In certain embodiments, the invention relates to a method of treating cancer in a subject in need thereof, comprising:
administering to the subject a therapeutically effective amount of any of the first compositions described herein wherein the first payload is an anti-cancer agent.

In certain embodiments, the invention relates to a method of treating cancer in a subject in need thereof, comprising:
administering to the subject a therapeutically effective amount of any of the first compositions described herein, wherein the first payload is an anti-cancer agent; and
administering to the subject a therapeutically effective amount of any of the second compositions described herein.

In certain embodiments, the invention relates to a method generating an image of a subject in need thereof, comprising:
administering to the subject a detectable amount of any of the first compositions described herein, wherein the first payload is an imaging agent; and
generating an image.

DETAILED DESCRIPTION

Overview

Figure 1:
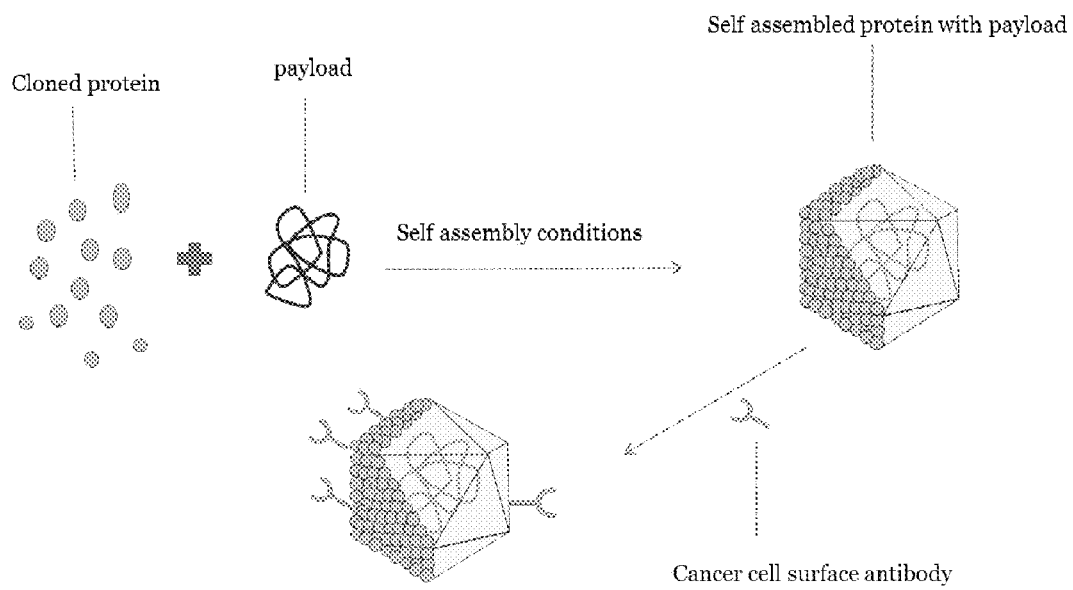
FIG. 1 depicts a schematic representation of an exemplary procedure for preparing a drug-loaded vehicle of the invention.
Figure 2:
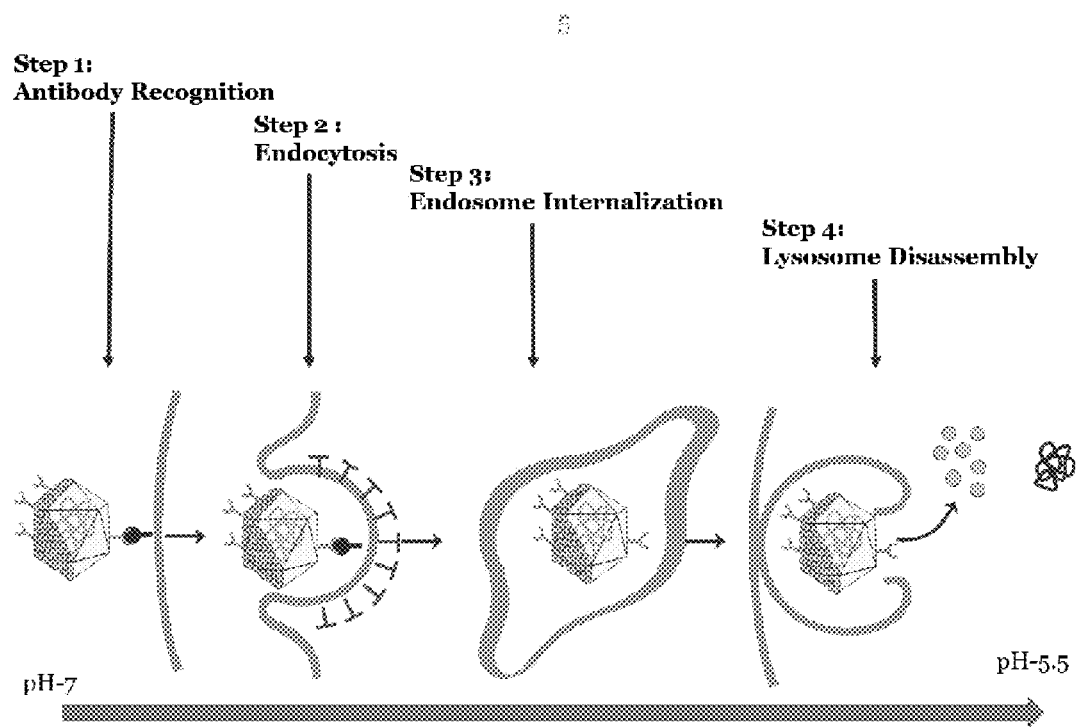
FIG. 2 depicts a schematic representation of a mechanism by which the drug-loaded vehicles may be internalized.
Figure 3:
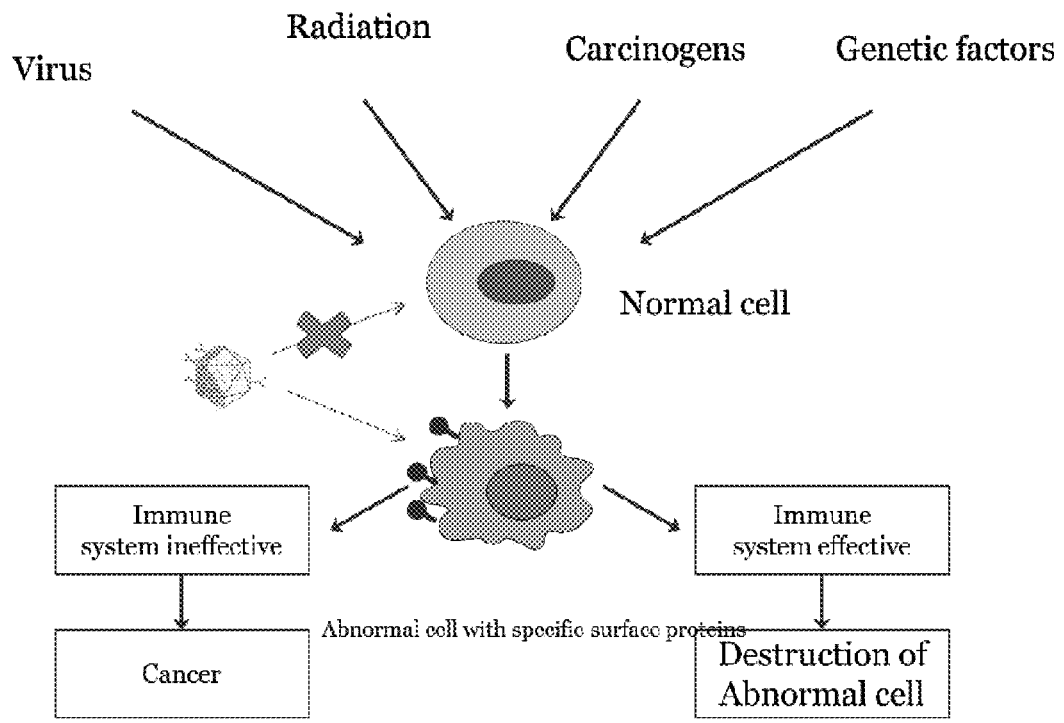
FIG. 3 depicts a schematic representation of the selectivity of the drug-loaded vehicles for cancer cells over normal healthy cells.

In certain embodiments, this invention relates to the use of self-assembling protein molecules for delivering a payload, for example, a toxic anti-cancer agent, a cancer immunotherapy, or an imaging agent, to specific tissues. In certain embodiments, the protein is clathrin or a derivative of clathrin. In certain embodiments, the protein is endogenous. In certain embodiments, the protein is non-immunogenic. In certain embodiments, the protein is ferritin or a derivative of ferritin.

In some embodiments, the self-assembled protein cages or vehicles, made of heavy and light chains, mask the toxicity of the anti-cancer agent, thereby resulting in decreased serum and systemic toxicity.

In certain embodiments, the heavy chain and the light chain are fused (e.g., the protein may be a fusion protein).

In other embodiments, the self-assembled delivery vehicles are used to target specific tissues, such as cancer cells, using antigen biomarkers, antibodies, or peptides that are recognized by the cell membrane of the target cell. In certain embodiments, once delivered to the target tissues, the clathrin cages are internalized by the cell for in-cell deposition of drug.

In certain embodiments, the payload is an anti-cancer agent, for example, a chemotherapeutic, siRNA, miRNA, immunotherapeutics, or a radiotherapeutic. In certain embodiments, the payload is an imaging agent, such as a contrast medium or a fluorophore. In certain embodiments, the drug is a radiotherapeutic, such as a radionuclide.

In certain embodiments, the payload is conjugated to the protein, for example, to the light chain. "Conjugated" or "linked" as used herein means ionically or, preferably, covalently attached (e.g., via a crosslinking agent).

In certain embodiments, the invention relates to a method of treating a subject in need thereof comprising administering to the subject a therapeutically effective amount of any one of the drug-loaded vehicles described herein. In certain embodiments, the drug-loaded vehicle is administered to the subject intravenously or intraperitoneally.

This technology is expected to achieve synergistic results as compared to the protein alone, the payload alone, the targeting agent alone, or any combination of two of these components. The advantages include, but are not limited to: 1. The proteins self-assemble following their loading with known or newly developed therapeutic agents. 2. The proteins are easily internalized by cells. 3. The assembled, drug-loaded vehicles are stable in serum proteins and are non-toxic while transported in vivo via the blood and lymph system. 4. The proteins and vehicles are designed to specifically target diseased cells using specific antibodies or high-affinity fragments of antibodies. In some embodiments, the antibodies are designed to enhance the immune system by uncovering a cancer call not identified by the immune system. 5. Once targeted to diseased cells, the delivery vehicles are internalized and during this process they disassemble and release their therapeutic agent and specifically kill the diseased cell or allow the immune system to fight it. 6. This platform has the potential to provide mono-, bi- and multi-specific targeting. 7. Because of the ease of internalization, if the payload is an imaging agent or a radiotherapeutic, the vehicles may be used for tumor imaging or radiotherapy. 8. For therapeutic applications where longer half-life is desired, the vehicles may be modified by increasing the molecular weight of the proteins or adding polymeric extensions. 9. The combination of (i) endogenous, self-assembled, cell-internalized proteins with (ii) self-internalized antibodies and (iii) payloads can improve cancer imaging or treatment while lowering systemic toxicity.

Exemplary Proteins

In certain embodiments, the invention relates to a protein having a heavy chain, wherein the heavy chain has greater than 85% sequence homology to SEQ ID NO:3. In certain embodiments, the invention relates to any of the proteins described herein, wherein the heavy chain has greater than 90% sequence homology to SEQ ID NO:3. In certain embodiments, the invention relates to any of the proteins described herein, wherein the heavy chain has greater than 95% sequence homology to SEQ ID NO:3. In certain embodiments, the invention relates to any of the proteins described herein, wherein the heavy chain has greater than 98% sequence homology to SEQ ID NO:3. In certain embodiments, the invention relates to any of the proteins described herein, wherein the heavy chain has greater than 99% sequence homology to SEQ ID NO:3. In certain embodiments, the invention relates to any of the proteins described herein, wherein the heavy chain has SEQ ID NO:3.

In certain embodiments, the invention relates to a protein having a light chain, wherein the light chain has greater than 85% sequence homology to SEQ ID NO:6. In certain embodiments, the invention relates to any of the proteins described herein, wherein the light chain has greater than 90% sequence homology to SEQ ID NO:6. In certain embodiments, the invention relates to any of the proteins described herein, wherein the light chain has greater than 95% sequence homology to SEQ ID NO:6. In certain embodiments, the invention relates to any of the proteins described herein, wherein the light chain has greater than 98% sequence homology to SEQ ID NO:6. In certain embodiments, the invention relates to any of the proteins described herein, wherein the light chain has greater than 99% sequence homology to SEQ ID NO:6. In certain embodiments, the invention relates to any of the proteins described herein, wherein the light chain has SEQ ID NO:6.

In certain embodiments, the invention relates to any of the proteins described herein, wherein the protein has a heavy chain and a light chain.

Exemplary Compositions

In certain embodiments, the invention relates to a first composition comprising, consisting essentially of, or consisting of a protein, a first payload, and a first targeting agent, wherein the protein is in the form of a three-dimensional cage structure comprising an outer surface and an inner cavity; and the first targeting agent is conjugated to the outer surface of the three-dimensional cage structure. In certain embodiments, the first targeting agent selectively targets cancer cells as compared to healthy cells. In certain embodiments, the first targeting agent specifically targets diseased cells, such as cancer cells.

In certain embodiments, the invention relates to a second composition comprising, consisting essentially of, or consisting of a protein, a second payload, and a second targeting agent, wherein the protein is in the form of a three-dimensional cage structure comprising an outer surface and an inner cavity; the second payload is an immunogen; and the second targeting agent conjugated to the outer surface of the three-dimensional cage structure. In certain embodiments, the second targeting agent does not selectively target cancer cells as compared to healthy cells.

In certain embodiments, the compositions (i.e., the first composition or the second composition) are able to identify or transfect cells in vivo.

Protein

In certain embodiments, the invention relates to any of the compositions described herein (e.g., the first composition or the second composition), wherein the protein is able to deliver a payload into a cell.

In certain embodiments, the invention relates to any of the compositions described herein (e.g., the first composition or the second composition), wherein the protein is clathrin or a clathrin derivative.

In certain embodiments, the invention relates to any of the compositions described herein (e.g., the first composition or the second composition), wherein the protein comprises a heavy chain or a light chain. In certain embodiments, the invention relates to any of the compositions described herein, wherein the protein comprises a heavy chain and a light chain. In some embodyments scaffolding of truncated clathrin and their repeated squances of these tranced peptides are used as payload carries of anticancer internalizing peptides.

In certain embodiments, the invention relates to any of the compositions described herein, wherein the heavy chain has a molecular weight from about 100 kDa to about 300 kDa. In certain embodiments, the invention relates to any of the compositions described herein, wherein the heavy chain has a molecular weight of about 100 kDa, about 110 kDa, about 120 kDa, about 130 kDa, about 140 kDa, about 150 kDa, about 160 kDa, about 170 kDa, about 180 kDa, about 190 kDa, about 200 kDa, about 210 kDa, about 220 Da, about 230 kDa, about 240 kDa, about 250 kDa, about 260 kDa, about 270 kDa, about 280 kDa, about 290 kDa, or about 300 kDa. In certain embodiments, the invention relates to any of the compositions described herein, wherein the heavy chain has a molecular weight of about 190 kDa.

In certain embodiments, the invention relates to any of the compositions described herein, wherein the heavy chain has greater than 85% sequence homology to SEQ ID NO:3. In certain embodiments, the invention relates to any of the compositions described herein, wherein the heavy chain has greater than 90% sequence homology to SEQ ID NO:3. In certain embodiments, the invention relates to any of the compositions described herein, wherein the heavy chain has greater than 95% sequence homology to SEQ ID NO:3. In certain embodiments, the invention relates to any of the compositions described herein, wherein the heavy chain has greater than 98% sequence homology to SEQ ID NO:3. In certain embodiments, the invention relates to any of the compositions described herein, wherein the heavy chain has greater than 99% sequence homology to SEQ ID NO:3. In certain embodiments, the invention relates to any of the compositions described herein, wherein the heavy chain has SEQ ID NO:3.

In certain embodiments, the invention relates to any of the compositions described herein, wherein the light chain has a molecular weight from about 15 kDa to about 45 kDa. In certain embodiments, the invention relates to any of the compositions described herein, wherein the light chain has a molecular weight of about 15 kDa, about 16 kDa, about 17 kDa, about 18 kDa, about 19 kDa, about 20 kDa, about 21 kDa, about 22 kDa, about 23 kDa, about 24 kDa, about 25 kDa, about 26 kDa, about 27 kDa, about 28 kDa, about 29 kDa, about 30 kDa, about 31 kDa, about 32 kDa, about 33 kDa, about 34 kDa, about 35 kDa, about 36 kDa, about 37 kDa, about 38 kDa, about 39 kDa, about 40 kDa, about 41 kDa, about 42 kDa, about 43 kDa, about 44 kDa, or about 45 kDa. In certain embodiments, the invention relates to any of the compositions described herein, wherein the light chain has a molecular weight of about 28 kDa.

In certain embodiments, the invention relates to any of the compositions described herein, wherein the light chain has greater than 85% sequence homology to SEQ ID NO:6. In certain embodiments, the invention relates to any of the compositions described herein, wherein the light chain has greater than 90% sequence homology to SEQ ID NO:6. In certain embodiments, the invention relates to any of the compositions described herein, wherein the light chain has greater than 95% sequence homology to SEQ ID NO:6. In certain embodiments, the invention relates to any of the compositions described herein, wherein the light chain has greater than 98% sequence homology to SEQ ID NO:6. In certain embodiments, the invention relates to any of the compositions described herein, wherein the light chain has greater than 99% sequence homology to SEQ ID NO:6. In certain embodiments, the invention relates to any of the compositions described herein, wherein the light chain has SEQ ID NO:6.

In certain embodiments, the invention relates to any of the compositions described herein, wherein the three-dimensional cage structure has a diameter from about 10 nm to about 100 nm. In certain embodiments, the invention relates to any of the compositions described herein, wherein the three-dimensional cage structure has a diameter of about 10 nm, about 20 nm, about 30 nm, about 40 nm, about 50 nm, about 60 nm, about 70 nm, about 80 nm, about 90 nm, or about 100 nm. In certain embodiments, the invention relates to any of the compositions described herein, wherein the three-dimensional cage structures have an average diameter from about 10 nm to about 100 nm. In certain embodiments, the invention relates to any of the compositions described herein, wherein the three-dimensional cage structures have an average diameter of about 10 nm, about 20 nm, about 30 nm, about 40 nm, about 50 nm, about 60 nm, about 70 nm, about 80 nm, about 90 nm, or about 100 nm. In certain embodiments, the diameter of the three-dimensional cage structures may be estimated or measured by techniques known in the art, such as dynamic light scattering or high-resolution NMR spectroscopy.

In certain embodiments, the invention relates to any of the compositions described herein, wherein the three-dimensional cage structure is substantially spherical.

In certain embodiments, the invention relates to any of the compositions described herein, wherein the three-dimensional cage structure is non-covalently assembled, for example, self-assembled.

In certain embodiments, the invention relates to any of the compositions described herein, wherein the three-dimensional cage structure is substantially stable at about 37° C. at about pH greater than or equal to 7.

In certain embodiments, the invention relates to any of the compositions described herein, wherein the three-dimensional cage structure is substantially stable at about 37° C. at about pH 7.

In certain embodiments, the invention relates to any of the compositions described herein, wherein the three-dimensional cage structure is substantially stable at about 37° C. at about pH 6.5 to about pH 8.5.

In certain embodiments, the invention relates to any of the compositions described herein, wherein the three-dimensional cage structure is substantially unstable at about 37° C. at about pH less than or equal to 5.5.

In certain embodiments, the invention relates to any of the compositions described herein, wherein the three-dimensional cage structure is substantially unstable at about 37° C. at about pH 5.5.

Cage-like proteins such as clathrin, ferritins, DNA-binding proteins (dps), and heat shock proteins have three distinct surfaces (inside, outside, interface) that can be exploited to generate nanomaterials with multiple functionality by design. Protein cages are biological in origin and each cage exhibits extremely homogeneous size distribution. This homogeneity can be used to attain a high degree of homogeneity of the templated material and its associated property. A series of protein cages exhibiting diversity in size, functionality, and chemical and thermal stabilities can be utilized for materials synthesis under a variety of conditions. Since synthetic approaches to materials science often use harsh temperature and pH, in certain embodiments, it can be an advantage to utilize protein cages from extreme environments, such as acidic thermal hot springs.

Protein cage architectures, 10-100 nm in diameter, are self-assembled hollow spheres derived from viruses and other biological cages, including heat shock proteins (Hsp), DNA-binding proteins from starved cells (Dps), and ferritins. These architectures play critical biological roles. For example, heat shock proteins are thought to act as chaperones that prevent protein denaturation, and ferritins are known to store iron (which is both essential and toxic) as a nanoparticle of iron oxide. While each of these structures has evolved to perform a unique natural function, they are similar in that they are all essentially proteinaceous containers with three distinct surfaces (interior, exterior, and subunit interface) to which one can impart function by design. Protein cage architectures have demonstrated utility in nanotechnology with applications including inorganic nanoparticle synthesis and the development of targeted therapeutic and imaging delivery agents.

Protein cage architectures are naturally diverse; each has unique attributes (including size, structure, solvent accessibility, chemical and temperature stability, structural plasticity, assembly and disassembly parameters, and electrostatics) useful to particular applications. Importantly, one can capitalize on these features or alter them via genetic or chemical modification. Atomic level structural information identifies the precise location of amino acids within protein cage architectures and in turn allows for the rational inclusion, exclusion, and substitution of amino acid(s) (at the genetic level) resulting in protein cages with novel functional properties.

Protein cages isolated from thermophilic environments are desirable as building blocks for nanotechnology due to their potential stability in harsh reaction conditions including high temperature and pH extremes. Interestingly, one of the most stable protein cage architectures, ferritin, is commonly found in mesophilic organisms, including animals, plants, and microbes. For example, horse spleen ferritin exhibits broad pH (pH 2-8) and temperature stability (<70° C.). Ferritins are involved in iron sequestration, which they accomplish through the oxidation of soluble Fe(II) using $O_2$. This oxidation results in the formation of a nanoparticle of $Fe_2O_3$ encapsulated (and rendered nontoxic) within the protein cage. High charge density on the inner surface of the protein cage promotes this reaction, which is assisted by an enzymatic (ferroxidase) activity in some ferritin subunits. Ferritins are made up of 24 subunits, which form a spherical cage 12 nm in diameter. The ferritin family also includes the 24 subunit bacterioferritins and the Dps class of proteins, which assemble from 12 monomers.

A cavity forming protein cage is described in U.S. Pat. No. 7,393,924 (incorporated by reference). The cage is formed in vitro from a plurality of 3-legged triskelia, each triskelion having 6 protein subunits; 3 Clathrin heavy chain and 3 Clathrin light chain subunits. In certain embodiments, the 3-legged triskelia are not required (see, e.g., U.S. Patent Application Publication No. 2015/0307570, incorporated by reference). For example, the protein may be an isolated, synthetic or recombinant, protein comprising in whole or in part one or more types of clathrin proteins of one or more isoforms, including cloned isoforms.

Payload

In certain embodiments, the invention relates to any of the first compositions described herein, wherein the payload is any therapeutic agent, but preferably an anti-cancer agent, such as paclitaxel, gemcitabine, or an azonafide (e.g., a compound described in U.S. Pat. No. 8,008,316, which is incorporated by reference).

As used herein, the terms "anti-cancer agent" and "therapeutic agent" are defined broadly as anything that cancer cells, including tumor cells, may be exposed to in a therapeutic protocol for the purpose of inhibiting their growth or kill the cells. In one embodiments, such agents can be used according to the compositions and methods described herein in conjunction with each other (e.g., LY294002 plus gemcitabine, taxol plus U0126, taxol plus gemcitabine, etc.), or in any combination thereof. Such agents include, but are not limited to, chemotherapeutic agents, such as anti-metabolic agents, e.g., Ara AC, 5-FU and methotrexate, antimitotic agents, e.g., TAXOL, inblastine and vincristine, alkylating agents, e.g., melphalan, BCNU and nitrogen mustard, topoisomerase II inhibitors, e.g., VW-26, topotecan and Bleomycin, strand-breaking agents, e.g., doxorubicin and DHAD, cross-linking agents, e.g., cisplatin and CBDCA, radiation and ultraviolet light.

As used herein, the term "chemotherapeutic agent" is intended to include chemical reagents which inhibit the growth of proliferating cells or tissues wherein the growth of such cells or tissues is undesirable. Particular chemotherapeutic agents include, but are not limited to (i) antimetabolites, such as cytarabine, fludarabine, 5-fluoro-2'-deoxyuridine, gemcitabine, hydroxyurea or methotrexate; (ii) DNAfragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, STI571 (CPG 57148B) or UCN-01 (7-hydroxystaurosporine); (x) enhancers of the AMPK signaling pathway, (xi) inhibitors of the PI3K/AKT/mTORC1 signaling pathway, (xii) inhibitors of the MEK/ERK signaling pathway, (xiii) miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xiv) hormones such as glucocorticoids or fenretinide; and (xv) hormone antagonists, such as tamoxifen, finasteride or LHRH antagonists. In an embodiment, the chemotherapeutic compound is one or more of gemcitabine, cisplatin, doxorubicin, daunarubicin, paclitaxel, taxotere and mitomycin C. In a particular embodiment, the chemotherapeutic compound is one or more of gemcitabine, cisplatin and paclitaxel.

Chemotherapeutic agents are well known in the art (see e.g., Gilman A. G., et al., The Pharmacological Basis of Therapeutics, 8th Ed., Sec 12:1202-1263 (1990)), and are typically used to treat neoplastic diseases. The chemotherapeutic agents generally employed in chemotherapy treatments are listed below in Table 1.

TABLE 1

| CLASS | TYPE OF AGENT | NONPROPRIETARY NAMES (OTHER NAMES) |
|---|---|---|
| Alkylating | Nitrogen Mustards | Mechlorethamine (HN$_2$) |
| | | Cyclophosphamide |
| | | Ifosfamide |
| | | Melphalan (L-sarcolysin) |
| | | Chlorambucil |
| | Ethylenimines And Methylmelamines | Hexamethylmelamine Thiotepa |
| | Alkyl Sulfonates | Busulfan |
| Alkylating | Nitrosoureas | Carmustine (BCNU) |
| | | Lomustine (CCNU) |
| | | Semustine (methyl-CCNU) |
| | | Streptozocin (streptozotocin) |
| | Triazenes | Decarbazine (DTIC; imethyltriazenoimi-dazolecarboxamide) |
| | Alkylator | cis-diamminedichloroplatinum II (CDDP) |
| Antimetabolites | Folic Acid Analogs | Methotrexate (amethopterin) |
| | Pyrimidine Analogs | Fluorouracil ('5-fluorouracil; 5-FU) |
| | | Floxuridine (fluorode-oxyuridine; FUdR) |
| | | Cytarabine (cytosine arabinoside) |
| | | gemcitabine (deoxycytidine analog) |
| | Purine Analogs and Related Inhibitors | Mercaptopuine (6-mercaptopurine; 6-MP) Thioguanine (6-thioguanine; TG) |
| | | Pentostatin (2'-deoxycoformycin) |
| Natural Products | Vinca Alkaloids | Vinblastin (VLB) |
| | | Vincristine |
| | Topoisomerase Inhibitors | Etoposide |
| | | Teniposide |
| | | Camptothecin |
| | | Topotecan |
| | | 9-amino-campotothecin CPT-11 |
| | Antibiotics | Dactinomycin (actinomycin D) |
| | | Adriamycin (Doxorubicin) |
| | | Daunorubicin (daunomycin; rubindomycin) |
| | | Doxorubicin |
| | | Bleomycin |
| | | Plicamycin (mithramycin) |
| | | Mitomycin (mitomycin C) |
| | | TAXOL (paclitaxel) |
| | | Taxotere |
| | Enzymes | L-Asparaginase |
| | Biological Response Modifiers | Interfon alfa interleukin 2 |
| Misc. Agents | Platinum Coordination Complexes | cis-diamminedichloroplatinum II (CDDP) Carboplatin |
| | | Oxaliplatin |
| | | Cisplatin |
| | Anthracendione | Mitoxantrone |
| | Substituted Urea | Hydroxyurea |
| | Methyl Hydraxzine Derivative | Procarbazine (N-methylhydrazine, (MIH) |
| | Adrenocortical Suppressant | Mitotane (o,p'-DDD) Aminoglutethimide |

TABLE 1-continued

| CLASS | TYPE OF AGENT | NONPROPRIETARY NAMES (OTHER NAMES) |
|---|---|---|
| Hormones and Antagonists | Adrenocorticosteroids | Prednisone |
| | | Dexamethasone |
| | Progestins | Hydroxyprogesterone Caproate |
| | | Medroxyprogesterone Acetate |
| | | Megestrol acetate |
| | Estrogens | Diethylstilbestrol |
| | | Ethinyl estradiol |
| | Antiestrogen | Tamoxifen |
| | Androgens | Testosterone propionate |
| | | Fluoxymesterone |
| | Antiandrogen | Flutamide |
| | Gonadotropin-releasing Hormone analog | Leuprolide |

In certain embodiments, the chemotherapeutic agents used in the compositions and methods can be a single agent or a combination of agents. Preferred combinations will include agents that have different mechanisms of action, e.g., the use of an anti-mitotic agent in combination with an alkylating agent.

In some embodiments, the anti-cancer agent is an inhibitor of ERK signaling, such as an inhibitor of MEK. As used herein, the term "inhibitor of MEK" refers to a compound or agent, such as a small molecule, that inhibits, decreases, lowers, or reduces the activity of MEK. Examples of inhibitors of MEK include, but are not limited to, AZD6244 (6-(4-Bromo-2-chloro-phenylamino)-7-fluoro-3-methyl-3H-benzoimidazole-5-carboxylic acid (2-hydroxy-ethoxy)-amide; selumetinib; Structure IV), and U0126 (1,4-diamino-2,3-dicyano-1,4-bis [2-aminophenylthio]butadiene; ARRY-142886; Structure V). Further non-limiting examples of MEK inhibitors include PD0325901, AZD2171, GDC-0973/XL-518, PD98059, PD184352, GSK1120212, RDEA436, RDEA119/BAY869766, AS703026, BIX 02188, BIX 02189, CI-1040 (PD184352), PD0325901, and PD98059. These and other inhibitors of MEK, as well as non-limiting examples of their methods of manufacture, are described in U.S. Pat. Nos. 5,525,625; 6,251,943; 7,820,664; 6,809,106; 7,759,518; 7,485,643; 7,576,072; 7,923,456; 7,732,616; 7,271,178; 7,429,667; 6,649,640; 6,495,582; 7,001,905; US Patent Publication No. US2010/0331334, US2009/0143389, US2008/0280957, US2007/0049591, US2011/0118298, International Patent Application Publication No. WO98/43960, WO99/01421, WO99/01426, WO00/41505, WO00/42002, WO00/42003, WO00/41994, WO00/42022, WO00/42029, WO00/68201, WO01/68619, WO02/06213 and WO03/077914, the contents of which are herein incorporated by reference in their entireties.

In another embodiment, the anti-cancer agent is an inhibitor of Epidermal Growth Factor Receptor (EGFR). EGFR is a member of the type 1 subgroup of receptor tyrosine kinase family of growth factor receptors which play critical roles in cellular growth, differentiation and survival. Activation of these receptors typically occurs via specific ligand binding which results in hetero- or homodimerization between receptor family members, with subsequent autophosphorylation of the tyrosine kinase domain. Specific ligands which bind to EGFR include epidermal growth factor (EGF), transforming growth factor alpha (TGF alpha), amphiregulin and some viral growth factors. Activation of EGFR triggers a cascade of intracellular signaling pathways involved in both cellular proliferation (the ras/raf/MAP kinase pathway) and survival (the PI3 kinase/Akt pathway). Members of this family, including EGFR and HER2, have been directly implicated in cellular transformation. A number of human malignancies are associated with aberrant or overexpression of EGFR and/or overexpression of its specific ligands. Aberrant or overexpression of EGFR has been associated with an adverse prognosis in a number of human cancers, including head and neck, breast, colon, prostate, lung (e.g., NSCLC, adenocarcinoma and squamous lung cancer), ovarian, gastrointestinal cancers (gastric, colon, pancreatic), renal cell cancer, bladder cancer, glioma, gynecological carcinomas and prostate cancer. In some instances, overexpression of tumor EGFR has been correlated with both chemoresistance and a poor prognosis. Mutations in EGFR are associated with many types of cancer as well. For example, EGFR mutations are highly prevalent in non-mucinous BAC patients. Finberg, et al., J. Mol. Diagnostics. (2007) 9(3):320-26. In an embodiment the EGFR inhibitor is an antibody such as Erbitutux™ (cetuximab, Imclone Systems Inc.) and ABX-EGF (panitumumab, Abgenix, Inc.). In another embodiment the EGFR inhibitor is a small molecule that competes with ATP such as Tarceva™ (erlotinib, OSI Pharmaceuticals), Iressa™ (gefitinib, Astra-Zeneca), tyrphostins described by Dvir, et al., J Cell Biol., 113:857-865 (1991); tricyclic pyrimidine compounds disclosed in U.S. Pat. No. 5,679,683; compound 6-(2,6-dichlorophenyl)-2-(4-(2-diethylaininoethoxy)phenylamino)-8-methyl-8H-pyrido(2,3-d)pyrimidin-7-one (known as PD166285) disclosed in Panek, et al., Journal of Pharmacology and Experimental Therapeutics 283, 1433-1444 (1997).

In addition to the specific agents described above, it is further contemplated that a polypeptide, an antibody or antigen binding fragment thereof, a toxin, an RNA interfering molecule, an siRNA molecule, and shRNA molecule, an antisense oligonucleotide, a peptide, a peptidomimetic, an aptamer, and the like, as well as combinations thereof, that appropriately enhance or inhibit the targets of pro-survival signaling pathways can also be used as a therapeutic agent according to the invention. In particular, the nucleic acid sequence, amino acid sequence, functional domain, structural domain, gene locus, and other identifying information for the signaling pathway targets described herein are well known in the art.

In certain embodiments, the payload is an siRNA moiety comprised of a sense strand and an antisense strand; the sense strand comprising a 3' end and a 5' end; and the antisense strand comprising a 3' end and a 5' end.

"Antisense" nucleic acids refer to nucleic acids that specifically hybridize (e.g., bind) with a complementary sense nucleic acid, e.g., cellular mRNA and/or genomic DNA, under cellular conditions so as to inhibit expression (e.g., by inhibiting transcription and/or translation). The binding may be by conventional base pair complementarity or, for example, in the case of binding to DNA duplexes, through specific interactions in the major groove of the double helix.

The siRNA moiety may further include a guanosine at the 5'-end.

The sense and/or antisense strands of the siRNA moiety may equal to or less than 30, 25, 24, 23, 22, 21, 20, 19, 18 or 17 nucleotides in length. An siRNA moiety may include one or more overhangs. For example, the siRNA moiety may include one or two 3' overhangs of 2-3 nucleotides. In certain embodiments, the invention relates to any of the compositions described herein, wherein the siRNA moiety is composed of 21-nt sense and 21-nt antisense strands, paired in a manner to have a 19-nucleotide duplex region and a 2-nt 3' overhang at each 3' terminus. In certain embodiments, the invention relates to any of the compositions describe herein, wherein the 2-nt 3' overhang is either UU or dTdT. Symmetric 3'-overhangs ensure that the sequence-specific endonuclease complexes (siRNPs) are formed with approximately equal ratios of sense and antisense target RNA cleaving siRNPs. The 3'-overhang in the sense strand provides no contribution to recognition as it is believed the antisense siRNA strand guides target recognition. Therefore, the UU or dTdT 3'-overhang of the antisense sequences is complementary to the target mRNA but the symmetrical UU or dTdT 3'-overhang of the sense siRNA oligo does not need to correspond to the mRNA. The use of deoxythymidines in both 3'-overhangs may increase nuclease resistance, although siRNA duplexes with either UU or dTdT overhangs work equally well. 2'-Deoxynucleotides in the 3' overhangs are as efficient as ribonucleotides, but are often cheaper to synthesize.

The targeted region in the mRNA, and hence the sequence in the siRNA duplex, are chosen using the following guidelines. The open reading frame (ORF) region from the cDNA sequence is recommended for targeting, preferably at least 50 to 100 nucleotides downstream of the start codon, most preferably at least 75-100. Both the 5' and 3' untranslated regions (UTRs) and regions near the start codon are not recommended for targeting as these may be richer in regulatory protein binding sites. UTR-binding proteins and/or translation initiation complexes may interfere with binding of the siRNP endonuclease complex.

The sequence of the mRNA or cDNA is searched seeking the sequence AA(N19)TT (SEQ ID NO: 8). Sequences with approximately 50% G/C-content (30% to 70%) are used. If no suitable sequences are found, the search is extended to sequences AA(N21). The sequence of the sense siRNA corresponds to 5'-(N19)dTdT-3' or N21, respectively. In the latter case, the 3' end of the sense siRNA is converted to dTdT. The rationale for this sequence conversion is to generate a symmetric duplex with respect to the sequence composition of the sense and antisense 3' overhangs. It is believed that symmetric 3' overhangs help to ensure that the siRNPs are formed with approximately equal ratios of sense and antisense target RNA-cleaving siRNPs. The modification of the overhang of the sense sequence of the siRNA duplex is not expected to affect targeted mRNA recognition, as the antisense siRNA strand glides target recognition.

If the target mRNA does not contain a suitable AA(N21) sequence, it is recommended to search for NA(N21) The sequence of the sense and antisense strand may still be synthesized as 5' (N19)TT as the sequence of the 3' most nucleotide of the antisense siRNA does not appear to contribute to specificity.

It is further recommended to search the selected siRNA sequence against EST libraries in appropriate databases (e.g., NCBI BLAST database search) to ensure that only one gene is targeted.

The appropriately designed siRNAs are either obtained from commercial sources (such as Dharmacon Research, Lafayette, Colo.; Xergon, Huntsville, Ala.; Ambion, Austin, Tex.) or chemically synthesized used appropriately protected ribonucleoside phosphoramidites and a conventional DNA/RNA synthesizer according to standard protocols. The RNA oligonucleotides are 2'-deprotected, desalted and the two strands annealed, according to manufacturer's specifications or conventional protocols, depending on how the siRNAs are obtained. All handling steps are conducted under strict sterile, RNase-free conditions.

In certain embodiments, linkers (also known as "linker molecules" or "cross-linkers" or "spacers") may be used to conjugate the payload to the protein. The majority of known cross-linkers react with amine, carboxyl, and sulfhydryl groups. Linker molecules may be responsible for different properties of the composition. The length of the linker should be considered in light of molecular flexibility during the conjugation step, and the availability of the conjugated molecule for its target. Longer linkers may thus improve the biological activity of the compositions of the invention, as well as the ease of preparation of them. The geometry of the linker may be used to orient a molecule for optimal reaction with a target. A linker with flexible geometry may allow the entire composition to conformationally adapt as it binds a target sequence. The nature of the linker may be altered for other various purposes. For example, the hydrophobicity of a polymeric linker may be controlled by the order of monomeric units along the polymer, e.g. a block polymer in which there is a block of hydrophobic monomers interspersed with a block of hydrophilic monomers.

The chemistry of preparing and utilizing a wide variety of molecular linkers is well-known in the art and many premade linkers for use in conjugating molecules are commercially available from vendors such as Pierce Chemical Co., Roche Molecular Biochemicals, United States Biological. Exemplary linker molecules for use in the compositions of the invention include, but are not limited to: aminocaproic acid (ACA); polyglycine, and any other amino acid polymer, polymers such as polyethylene glycol (PEG), polymethyl methacrylate (PMMA), polypropylene glycol (PPG); homobifunctional reagents such as APG, AEDP, BASED, BMB, BMDB, BMH, BMOE, BM[PEO]3, BM[PEO]4, BS3, BSOCOES, DFDNB, DMA, DMP, DMS, DPDPB, DSG, DSP (Lomant's Reagent), DSS, DST, DTBP, DTME, DTSSP, EGS, HBVS, Sulfo-BSOCOES, Sulfo-DST, Sulfo-EGS; heterobifunctional reagents such as ABH, AEDP, AMAS, ANB-NOS, APDP, ASBA, BMPA, BMPH, BMPS, EDC, EMCA, EMCH, EMCS, KMUA, KMUH, GMBS, LC-SMCC, LC-SPDP, MBS, MBuS, M2C2H, MPBH, MSA, NHS-ASA, PDPH, PMPI, SADP, SAED. SAND, SANPAH, SASD, SATP, SBAP, SFAD, SIA, SIAB, SMCC, SMPB, SMPH, SMPT, SPDP, Sulfo-EMCS, Sulfo-GMBS, Sulfo-HSAB, Sulfo-KMUS, Sulfo-LC-SPDP, Sulfo-MBS. Sulfo-NHS-LC-ASA, Sulfo-SADP, Sulfo-SANPAH, Sulfo-SIAB, Sulfo-SMCC, Sulfo-SMPB, Sulfo-LC-SMPT, SVSB, TFCS; and trifunctional linkers such as Sulfo-SBED.

Branched linkers may be prepared or used so that multiple moieties per linker are able to react. Such multiply reactive linkers allow the creation of multimeric binding sites.

An appropriate linker may be a macromolecular polymer. Any of the above-mentioned polymers may comprise the macromolecular polymer. In certain embodiments, such macromolecular polymers may be comprised entirely of one type of polymeric molecule. In other embodiments, the macromolecular polymers may be comprised of more than one type of polymeric molecule. The macromolecular polymers may exist in many possible structures, for example, linear, comb-branched, dendrigraft, dendrimer, or a linear dendron architectural copolymer. For example, PEG and PPG may be used to create a variety of bi- and multivalent linkers. Methods of synthesizing, activating, and modifying branched PEG/PPG polymers and PEG/PPG block co-polymers are well-known in the art. PEG is hydrophilic, while PPG is hydrophobic. For instance, a linker could be synthesized with a PPG core and PEG branches.

In certain embodiments, the invention relates to any of the first compositions described herein, wherein the payload is an imaging agent or a diagnostic agent. For example, the imaging agent may be a fluorescent imaging agent, such as a fluorophore or a gadolinium chelator, or a magnetic imaging agent, such as a magnetite mineral, a paramagnetic metal ion, or a metal chelating peptide. The imaging agent may be bound to an endogenous site (e.g., a paramagnetic metal ion), bound to a chemically modified site (e.g., chemical modifications to covalently bind a fluorophore or a gadolinium chelator), or genetically incorporated (e.g., a metal chelating peptide).

Examples of imaging or diagnostic agents include fluorophores (e.g. Dy547), chromophores, chemoluminescing agents, radionuclides (e.g., In-111, Tc-99m, I-123, I-125 F-18, Ga-67, Ga-68) for Positron Emission Tomography (PET) and Single Photon Emission Tomography (SPECT), unpair spin atoms and free radicals (e.g., Fe, lanthanides, and Gd), and contrast agents (e.g., chelated (DTPA) manganese) for Magnetic Resonance Imaging (MRI).

Additional examples include radionuclides (e.g. F-18, I-124, I-123, I-125, I-131, Re-186, Re-188, Y-90, Bi-212, At-211, Sr-89, Ho-166, Sm-153, Cu-67, Cu-64, In-111, Tc-99m, Ga-67, and Ga-68).

In certain embodiments, the invention relates to any of the second compositions described herein, wherein the payload is an immunogen, for example, an immunogenic antigen. An immunogen is an antigen or any substance that may be specifically bound by components of the immune system (e.g., antibody, lymphocytes). An immunogen is capable of inducing humoral or cell-mediated immune response rather than immunological tolerance. For example, the immunogen may be selected from the group consisting of keyhole limpet hemocyanin (KLH), concholepas concholepas hemacyanin (CCH), bovine serum albumin (BSA), and ovalbumin (OVA). Further information may be found in Chen D S, et al. Immunity. 2013; 39:1-10; and Chen D S, et al. Clin Cancer Res. 2012; 18:6580-6587 (both incorporated by reference).

In certain embodiments, the invention relates to any of the second compositions described herein, wherein the payload is an adjuvant. In certain embodiments, the invention relates to any of the second compositions described herein, wherein the payload is an immunogen and an adjuvant. recruiting of professional antigen-presenting cells (APCs) to the site of antigen exposure; increasing the delivery of antigens by delayed/slow release (depot generation); immunomodulation by cytokine production (selection of Th1 or Th2 response); inducing T-cell response (prolonged exposure of peptide-MHC complexes [signal 1] and stimulation of expression of T-cell-activating co-stimulators [signal 2] on the APCs' surface) and targeting (e. g. carbohydrate adjuvants which target lectin receptors on APCs). Examples of adjuvants include, but are not limited to Freund's Complete Adjuvant, lipopolysaccharides, muramyldipeptide from TB, synthetic polynucleotides, aluminum hydroxide, aluminum phosphate, cytokines, and squalene.

Targeting Agent

In certain embodiments, the invention relates to any of the compositions described herein, wherein the composition is a cell-specific therapeutic and imaging-agent delivery system. Targeted therapeutic delivery systems can enhance the effective dose at the site, such as a tumor, while decreasing general exposure to the drug and its associated side effects.

Figure 6:
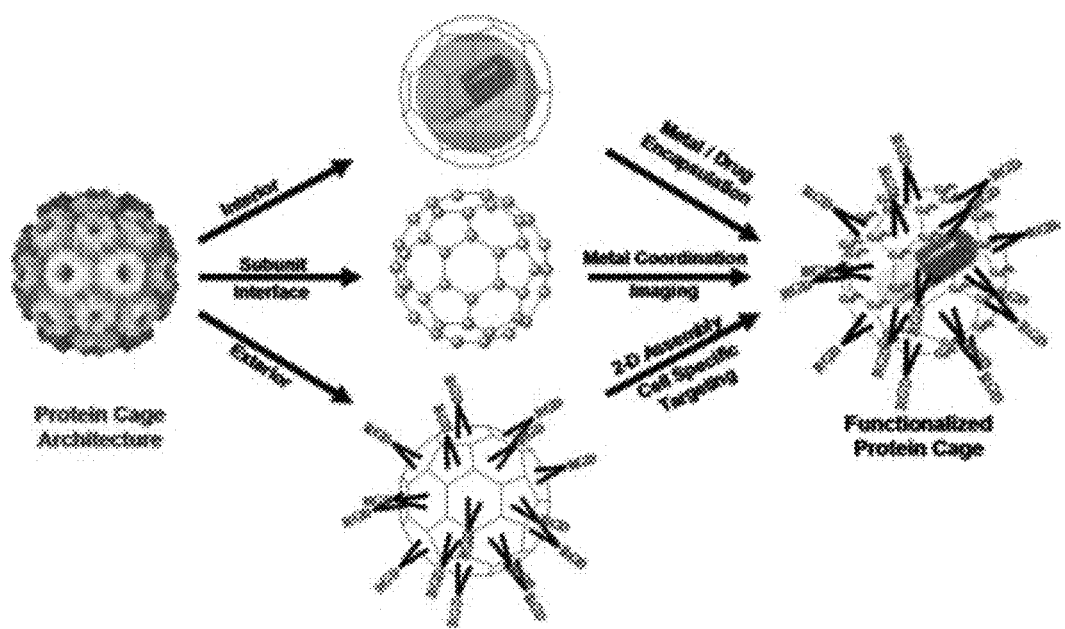
FIG. 6 depicts a schematic representation of protein cage functionalization. Protein cage architectures have three surfaces (interior, subunit interface, and exterior) amenable to both genetic and chemical modification.
Figure 7:
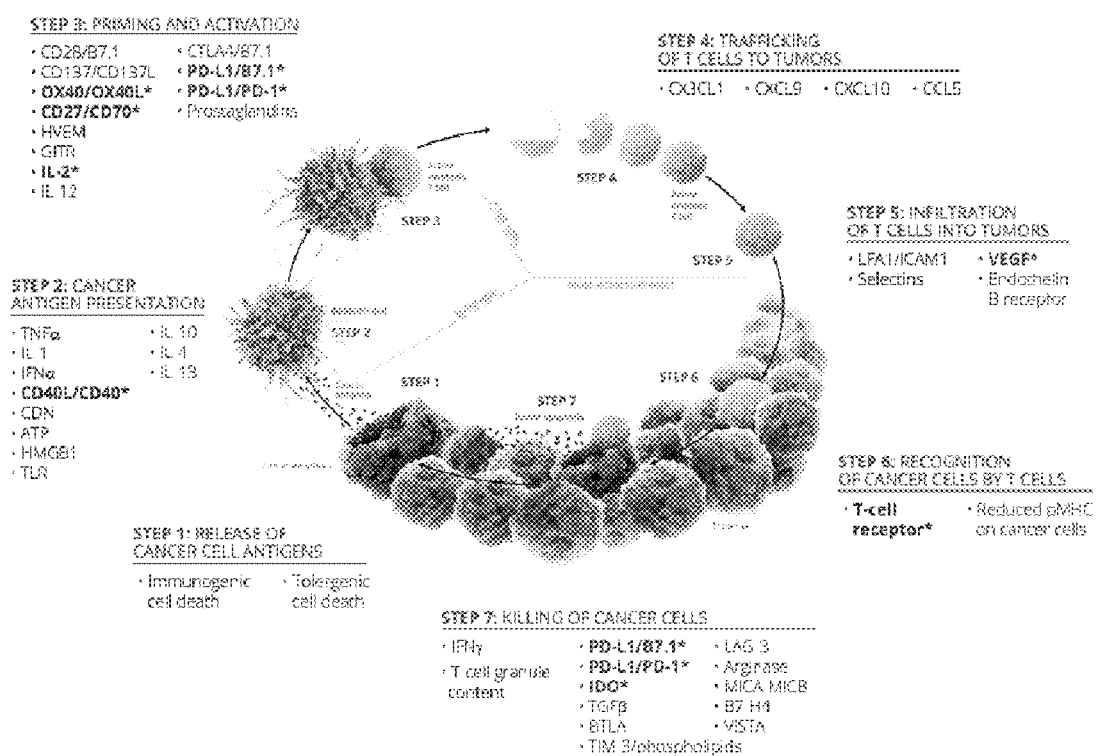
FIG. 7 depicts a schematic representation of the steps and components involved in cancer immunotherapy.

Protein cage architectures have three surfaces (interior, subunit interface, and exterior) amenable to both genetic and chemical modification. Each surface can play a distinct role in the development of new targeted therapeutic and imaging agent delivery systems. See FIG. 6. The cage interior can house therapeutics, the subunit interface incorporates gadolinium (an MRI contrast agent) and the exterior presents cell-specific targeting ligands (such as peptides and antibodies).

Protein cages have many beneficial attributes that are useful in their development as targeted therapeutic and imaging agent delivery systems. Their size falls into the nanometer range shown to localize in tumors due to the enhanced permeability and retention effect. Their multivalent nature enables the incorporation of multiple functionalities (including targeting peptides and imaging agents) on a single protein cage. They are malleable to both chemical and genetic manipulation and can be produced in heterologous expression systems (including bacterial, yeast, and baculoviral systems). In addition, detailed atomic resolution structural information enables the rational design of genetic mutants with specific functions, including cell-specific targeting.

Another key component for the development of protein cage architectures as imaging and therapeutic agents is cell-specific targeting. In vivo application of the phage display library technique enabled the identification of peptides that bind specifically to the vasculature of particular organs as well as tumors. One of the most characterized of these targeting peptides is RGD-4C (CDCRGDCFC (SEQ ID NO: 9)), which binds $\alpha_v\beta_3$ and $\alpha_v\beta_5$ integrins that are more prevalently expressed within tumor vasculature. For example, RGD-4C and other targeting peptides may be incorporated on the exteriors of the proteins. Fluorescein labeling of cell-specific targeted cages enables their visualization by epifluorescence microscopy. In addition to genetic incorporation, cell-specific targeting ligands, including antibodies and peptides, have also been chemically coupled to protein cage platforms. For example, an anti-CD4 monoclonal antibody conjugated to a protein could enable targeting of $CD4^+$ lymphocytes within a population of splenocytes. The multivalent nature of protein cage architectures results in the presentation of multiple targeting ligands on their surfaces and may potentially aid in the interaction of these protein cages with many surfaces including receptors on a variety of cell types.

In certain embodiments, the invention relates to any of the compositions described herein, wherein the targeting agent is an anti-PD-1 antibody.

A targeting agent, or affinity reagent, is a molecule that binds to an antigen or receptor or other molecule. In some embodiments, a targeting agent is a molecule that specifically binds to an antigen or receptor or other molecule. In certain embodiments, some or all of a targeting agent is composed of amino acids (including natural, non-natural, and modified amino acids), nucleic acids, or saccharides. In certain embodiments, a targeting agent is a small molecule.

Targeting agents in certain embodiments of the invention specifically bind to molecules or targets, such as a cell surface antigen, a cell surface receptor, or other cell surface molecule.

In some embodiments, the targeting agent is proteinaceous and may be present in a single peptide or polypeptide chain. In some embodiments, the polypeptide chain is a bispecific antibody.

Bispecific antibodies are well-established in the art as a Standard technique to create a single polypeptide that binds to two different determinants. Bispecific antibodies may be made in many different formats, including but not limited to quadroma, F(ab')2, tetravalent, heterodimeric scFv, bispecific scFv, tandem scFv, diabody and minibody formats, or scFvs appended to or recombinantly fused with whole antibodies.

Antibodies for use in the invention may be raised through any conventional method, such as through injection of immunogen into mice and subsequent fusions of lymphocytes to create hybridomas. Such hybridomas may then be used either (a) to produce antibody directly, which is purified and used for chemical conjugation to create a bispecific antibody, or (b) to clone cDNAs encoding antibody fragments for subsequent genetic manipulation. To illustrate one method employing the latter strategy, mRNA is isolated from the hybridoma cells, reverse-transcribed into cDNA using antisense oligo-dT or immunoglobulin gene-specific primers, and cloned into a plasmid vector. Clones are sequenced and characterized. They may then be engineered according to standard protocols to combine the heavy and light chains of each antibody, separated by a short peptide linker, into a bacterial or mammalian expression vector as previously described to produce a recombinant bispecific antibody, which are then expressed and purified according to well-established protocols in bacteria or mammalian cells. Antibodies, or other proteinaceous affinity molecules or targeting agents such as peptides, may also be created through display technologies that allow selection of interacting affinity reagents through the screening of very large libraries of, for example, immunoglobulin domains or peptides expressed by bacteriophage. Antibodies may also be humanized through grafting of human immunoglobulin domains, or made from transgenic mice or bacteriophage libraries that have human immunoglobulin genes/cDNAs.

In some embodiments, a targeting agent may comprise proteinaceous structures other than antibodies that are able to bind to protein targets specifically, including but not limited to avimers, ankyrin repeats and adnectins, and other such proteins with domains that can be evolved to generate specific affinity for antigens, collectively referred to as "antibody-like molecules." Modifications of proteinaceous affinity reagents through the incorporation of unnatural amino acids during synthesis may be used to improve their properties. Such modifications may have several benefits, including the addition of chemical groups that facilitate subsequent conjugation reactions.

In some embodiments, the targeting agent may be a peptide. In some embodiments, the peptide chain is a bispecific peptide. Peptides can readily be made and screened to create affinity reagents that recognize and bind to macromolecules such as proteins.

Bispecific affinity reagents may be constructed by separate synthesis and expression of the first and second affinity reagents. A polypeptide bispecific reagent can be expressed as two separately encoded chains that are linked by disulfide bonds during production in the same host cell, such as, for example, a bispecific scFv or diabody. Similarly, standard and widely used solid-phase peptide synthesis technology can be used to synthesize peptides, and chimeric bispecific peptides are well known in the art. A bispecific peptide strategy may be used to combine the first and second first and second affinity reagents in a single peptide chain. Alternatively, polypeptide chains or peptide chains can be expressed/synthesized separately, purified and then conjugated chemically to produce the bispecific affinity reagents useful in the compositions and methods described herein. Many different formats of antibodies may be used. Whole antibodies, $F(ab')_2$, F(ab'), scFv, as well as smaller Fab and single-domain antibody fragments may all be used to create the first and second affinity reagents. Following their expression and purification, the targeting agents can be chemically conjugated to the protein vehicle. Many conjugation chemistries may be used to effect this conjugation, including homofunctional or heterofunctional linkers that yield ester, amide, thioether, carbon-carbon, or disulfide linkages.

In some embodiments, the targeting agent is a peptide aptamer. A peptide aptamer is a peptide molecule that specifically binds to a target protein, and interferes with the functional ability of that target protein. Peptide aptamers consist of a variable peptide loop attached at both ends of a protein scaffold. Such peptide aptamers can often have a binding affinity comparable to that of an antibody (nanomolar range). Due to the highly selective nature of peptide aptamers, they can be used not only to target a specific protein, but also to target specific functions of a given protein (e.g., a signaling function).

Peptide aptamers are usually prepared by selecting the aptamer for its binding affinity with the specific target from a random pool or library of peptides. Peptide aptamers can be isolated from random peptide libraries by yeast two-hybrid screens. They can also be isolated from phage libraries or chemically generated peptides/libraries.

In some embodiments, the targeting agent is a nucleic acid aptamer. Nucleic acid aptamers are nucleic acid oligomers that bind other macromolecules specifically; such aptamers that bind specifically to other macromolecules can be readily isolated from libraries of such oligomers by technologies such as SELEX.

In some embodiments, the targeting agent is an oligosaccharide. Certain oligosaccharides are known ligands for certain extracellular or cell surface receptors.

The targeting agent recognizes a cell surface antigen on the target cell. The targeting agent may be an antibody, antibody-like molecule, or a peptide, such as an integrin-binding RGD peptide, or a small molecule, such as vitamins, e.g., folate, sugars such as lactose and galactose, or other small molecules. The cell surface antigen may be any cell surface molecule that undergoes internalization, such as a protein, sugar, lipid head group or other antigen on the cell surface. Examples of cell surface antigens useful in the context of the invention include but are not limited to the transferrin receptor type 1 and 2, the EGF receptor, HER2/Neu, VEGF receptors, integrins, CD33, CD19, CD20, CD22 and the asialoglycoprotein receptor.

Following their expression/synthesis and purification, the targeting agents are associated with the protein (for example, the heavy chain or the light chain of clathrin) through a covalent coupling, either through recombinant fusion, or chemical conjugation or association.

In certain embodiments, the targeting agent is an HER-2-targeting antibody, for example, trastuzumab or pertuzumab.

In certain embodiments, the targeting agent is an EGFR-targeting antibody, such as IMC-225.

In certain embodiments, the targeting agent is a VEGFR-2-targeting antibody.

In certain embodiments, the targeting agent is a CD-20-targeting antibody.

In certain embodiments, the targeting agent is a CD-22-targeting antibody.

In certain embodiments, the targeting agent is a CD-4-targeting antibody.

Exemplary Methods of Therapy or Diagnostic Imaging

One aspect of the invention relates to a method of treating cancer in a subject in need thereof, comprising:

administering to the subject a therapeutically effective amount of any one of the first compositions described herein wherein the first payload is an anti-cancer agent.

One aspect of the invention relates to a method of treating cancer in a subject in need thereof, comprising:

administering to the subject a therapeutically effective amount of any one of the first compositions described herein wherein the first payload is an anti-cancer agent; and administering to the subject a therapeutically effective amount of any one of the second compositions described herein.

The language "effective amount" of a targeted therapeutic agent refers to that amount necessary or sufficient to eliminate, reduce, or maintain (e.g., prevent the spread of) a tumor, or other target. The effective amount can vary depending on such factors as the disease or condition being treated, the particular targeted constructs being administered, the size of the subject, or the severity of the disease or condition. One of ordinary skill in the art can empirically determine the effective amount of a particular composition without undue experimentation.

In certain embodiments, the invention relates to any of the methods described herein, wherein the cancer is lung cancer. In certain embodiments, the invention relates to any of the methods described herein, wherein the cancer is non-small cell lung cancer (NSCLC).

In certain embodiments, the invention relates to any of the methods described herein, wherein the cancer is pancreatic cancer.

In certain embodiments, the invention relates to any of the methods described herein, wherein the first composition and the second composition are co-administered, i.e., wherein the first composition and the second composition are administered sequentially, simultaneously, or separately.

In certain embodiments, the invention relates to any of the methods described herein, wherein the first composition and the second composition are administered simultaneously, for example, in one pharmaceutical formulation.

Another aspect of the invention relates to a method generating an image of a subject in need thereof, comprising:

administering to the subject a detectable amount of any of the first compositions described herein wherein the first payload is an imaging agent or a diagnostic agent; and generating an image.

The language "effective amount" of a targeted imaging agent refers to that amount necessary or sufficient to visualize a tumor, or other target. The effective amount can vary depending on such factors as the cells or tissue being imaged, the particular targeted constructs being administered, the size of the subject, or the severity of the disease or condition. One of ordinary skill in the art can empirically determine the effective amount of a particular composition without undue experimentation.

In certain embodiments, the invention relates to any one of the methods described herein, wherein the subject is a mammal; preferably, the subject is a human.

Exemplary Pharmaceutical Compositions

In another aspect, the invention provides pharmaceutically acceptable compositions which comprise a therapeutically-effective amount of one or more of the compositions described above, formulated together with one or more pharmaceutically acceptable carriers (additives) and/or diluents. As described in detail below, the pharmaceutical compositions of the invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

As set out above, certain embodiments of the compositions may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of components of the compositions of the invention. These salts can be prepared in situ in the administration vehicle or the dosage form manufacturing process, or by separately reacting a purified compound in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject components include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, components of the compositions of the invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of components of the compositions of the invention. These salts can likewise be prepared in situ in the administration vehicle or the dosage form manufacturing process, or by separately reacting the purified component in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the composition which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the invention comprises an excipient selected from the group consisting of cyclodextrins, celluloses, liposomes, micelle forming agents, e.g., bile acids, and polymeric carriers, e.g., polyesters and polyanhydrides; and a compound of the invention. In certain embodiments, an aforementioned formulation renders orally bioavailable a composition of the invention.

Methods of preparing these formulations or compositions include the step of bringing into association a composition of the invention with the carrier and, optionally, one or more accessory ingredients. In general, the formulations are prepared by uniformly and intimately bringing into association a composition of the invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a composition of the invention as an active ingredient. A composition of the invention may also be administered as a bolus, electuary or paste.

In solid dosage forms of the invention for oral administration (capsules, tablets, pills, dragees, powders, granules, trouches and the like), the composition is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical formulation may also comprise buffering agents. Solid formulations of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered composition moistened with an inert liquid diluent.

The tablets, and other solid dosage forms of the pharmaceutical formulations of the invention, such as dragees, capsules, pills and granules, may optionally be scored or prepared with coatings and shells, such as enteric coatings and other coatings well known in the pharmaceutical-formulating art. They may also be formulated so as to provide slow or controlled release of the composition or the payload therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These formulations may also optionally contain opacifying agents and may be formulated so that they release the active ingredient(s) only, or preferentially, in a certain portion of the gastrointestinal tract, optionally, in a delayed manner Examples of embedding compositions which can be used include polymeric substances and waxes. The active ingredient can also be in micro-encapsulated form, if appropriate, with one or more of the above-described excipients.

Liquid dosage forms for oral administration of the compositions of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral formulations can also include adjuvants such as wetting agents, emulsifying and suspending agents, sweetening, flavoring, coloring, perfuming and preservative agents.

Suspensions, in addition to the compositions, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration of a composition of this invention include powders, sprays, ointments, pastes, creams, lotions, gels, solutions, patches and inhalants. The composition may be mixed under sterile conditions with a pharmaceutically-acceptable carrier, and with any preservatives, buffers, or propellants which may be required.

Pharmaceutical formulations of this invention suitable for parenteral administration comprise one or more compositions of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical formulations of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These formulations may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compositions of the invention are administered as pharmaceuticals, to humans and animals, they can be given per se or as a pharmaceutical formulation containing, for example, 0.1 to 99% (more preferably, 10 to 30%) of composition in combination with a pharmaceutically acceptable carrier.

The formulations of the invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

These formulations may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compositions of the invention, which may be used in a suitable hydrated form, and/or the pharmaceutical formulations of the invention, are formulated into pharmaceutically-acceptable dosage forms by conventional methods known to those of skill in the art.

Actual dosage levels of the active ingredients in the pharmaceutical formulations of this invention may be varied so as to obtain an amount of the payload which is effective to achieve the desired therapeutic response for a particular patient, composition, and mode of administration, without being toxic to the patient.

The selected dosage level will depend upon a variety of factors including the activity of the particular composition of the invention employed, or the ester, salt or amide thereof, the route of administration, the time of administration, the rate of excretion or metabolism of the particular composition being employed, the rate and extent of absorption, the duration of the treatment, other drugs, compositions and/or materials used in combination with the particular composition employed, the age, sex, weight, condition, general health and prior medical history of the patient being treated, and like factors well known in the medical arts.

A physician or veterinarian having ordinary skill in the art can readily determine and prescribe the effective amount of the pharmaceutical formulation required. For example, the physician or veterinarian could start doses of the compositions of the invention employed in the pharmaceutical formulation at levels lower than that required in order to achieve the desired therapeutic effect and gradually increase the dosage until the desired effect is achieved.

In general, a suitable daily dose of a composition of the invention will be that amount of the composition that is the lowest dose effective to produce a therapeutic effect. Such an effective dose will generally depend upon the factors described above.

If desired, the effective daily dose of the composition may be administered as two, three, four, five, six or more sub-doses administered separately at appropriate intervals throughout the day, optionally, in unit dosage forms. Preferred dosing is one administration per day.

While it is possible for a composition of the invention to be administered alone, it is preferable to administer the composition as a pharmaceutical formulation.

The composition according to the invention may be formulated for administration in any convenient way for use in human or veterinary medicine, by analogy with other pharmaceuticals.

In another aspect, the invention provides pharmaceutically acceptable formulations that comprise a therapeutically-effective amount of one or more of the subject compositions, as described above, formulated together with one or more pharmaceutically acceptable carriers (additives) and/or diluents. As described in detail below, the pharmaceutical formulations of the invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The patient receiving this treatment is any animal in need, including primates, in particular humans, and other mammals such as equines, cattle, swine and sheep; and poultry and pets in general.

Conjunctive or combination therapy, thus includes sequential, simultaneous and separate administration of the compositions in a way that the therapeutical effects of the first administered one is not entirely disappeared when the subsequent is administered.

Exemplary Kits

In certain embodiments, the invention relates to a kit for treating or imaging cancer. For example, a kit may comprise one or more compositions as described above and optionally instructions for their use; preferably the kit comprises a first composition and a second composition. In still other embodiments, the invention provides kits comprising one or more pharmaceutical or diagnostic formulations and/or one or more devices for accomplishing administration. For example, a subject kit may comprise a pharmaceutical or diagnostic formulation and catheter for accomplishing direct injection.

EXEMPLIFICATION

The invention now being generally described, it will be more readily understood by reference to the following examples which are included merely for purposes of illustration of certain aspects and embodiments of the invention, and are not intended to limit the invention.

Example 1—Expression of Clathrin Heavy Chain

Clathrin human isoform 2 heavy chain was optimized for an *E. coli* expression system as follows:

```
(SEQ ID NO: 1):
MAQILPIRFQEHLQLQNLGINPANIGFSTLTMESDKFICIREKVGEQAQVVIIDMNDPS

NPIRRPISADSAIMNPASKVIALKAGKTLQIFNIEMKSKMKAHTMTDDVTFWKWISLNT

VALVTDNAVYHWSMEGESQPVKMFDRHSSLAGCQIINYRTDAKQKWLLLTGISAQQNRV

VGAMQLYSVDRKVSQPIEGHAASFAQFKMEGNAEESTLFCFAVRGQAGGKLHIIEVGTP

PTGNQPFPKKAVDVFFPPEAQNDFPVAMQISEKHDVVFLITKYGYIHLYDLETGTCIYM

NRISGETIFVTAPHEATAGIIGVNRKGQVLSVCVEEENIIPYITNVLQNPDLALRMAVR

NNLAGAEELFARKFNALFAQGNYSEAAKVAANAPKGILRTPDTIRRFQSVPAQPGQTSP

LLQYFGILLDQGQLNKYESLELCRPVLQQGRKQLLEKWLKEDKLECSEELGDLVKSV

DPTLALSVYLRANVPNKVIQCFAETGQVQKIVLYAKKVGYTPDWIFLLRNVMRISPDQG

QQFAQMLVQDEEPLADITQIVDVFMEYNLIQQCTAFLLDALKNNRPSEGPLQTRLLEMN

LMHAPQVADAILGNQMFTHYDRAHIAQLCEKAGLLQRALEHFTDLYDIKRAVVHTHLLN

PEWLVNYFGSLSVEDSLECLRAMLSANIRQNLQICVQVASKYHEQLSTQSLIELFESFK

SFEGLFYFLGSIVNFSQDPDVHFKYIQAACKTGQIKEVERICRESNCYDPERVKNFLKE

AKLTDQLPLIIVCDRFDFVHDLVLYLYRNNLQKYIEIYVQKVNPSRLPVVIGGLLDVDC

SEDVIKNLILVVRGQFSTDELVAEVEKRNRLKLLLPWLEARIHEGCEEPATHNALAKIY

IDSNNNPERFLRENPYYDSRVVGKYCEKRDPHLACVAYERGQCDLELINVCNENSLF

KSLSRYLVRRKDPELWGSVLLESNPYRRPLIDQVVQTALSETQDPEEVSVTVKAFMTAD

LPNELIELLEKIVLDNSVFSEHRNLQNLLILTAIKADRTRVMEYINRLDNYDAPDIANI

AISNELFEEAFAIFRKFDVNTSAVQVLIEHIGNLDRAYEFAERCNEPAVWSQLAKAQLQ

KGMVKEAIDSYIKADDPSSYMEVVQAANTSGNWEELVKYLQMARKKARESYVETELIFA

LAKTNRLAELEEFINGPNNAHIQQVGDRCYDEKMYDAAKLLYNNVSNFGRLASTLVHLG

EYQAAVDGARKANSTRTWKEVCFACVDGKEFRLAQMCGLHIVVHADELEELINYYQDRG

YFEELITMLEAALGLERAHMGMFTELAILYSKFKPQKMREHLELFWSRVNIPKVLRAAE

QAHLWAELVFLYDKYEEYDNAIITMMNHPTDAWKEGQFKDIITKVANVELYYRAIQF
```

YLEFKPLLLNDLLMVLSPRLDHTRAVNYFSKVKQLPLVKPYLRSVQNHNNKSVNESLNL

FITEEDYQALRTSIDAYDNFDNISLAQRLEKHELIEFRRIAAYLFKGNNRWKQSVELCK

KDSLYKDAMQYASESKDTELAEEELLQWFLQEEKRECFGACLFTCYDLLRPDVVLETAWR

HNIMDFAMPYFIQVMKEYLTKVDKLDASESLRKEEEQATETQPIVYGNLSL (SEQ ID NO: 2):
ATGGCGCAGATCCTGCCGATTCGCTTCCAGGAACACCTGCAaCTGCAaAACCTGGGCAT

CAACCCGGCAAACATCGGTTTCTCTACCCTGACtATGGAGTCTGATAAGTTTATCTGTA

TCCGTGAGAAAGTGGGTGAGCAGGCTCAGGTGGTGATTATTGACATGAACGACCCGTCT

AACCCGATCCGTCGCCCGATCTCCGCAGATTCCGCAATCATGAACCCGGCGTCCAAGGT

TATCGCGCTGAAAGCTGGTAAGACCCTGCAaATCTTTAACATTGAGATGAAGTCCAAAA

TGAAGGCGCATACCATGACCGACGACGTTACCTTCTGGAAGTGGATCTCTCTGAACACC

GTTGCACTGGTTACTGACAACGCGGTGTACCACTGGTCTATGGAAGGTGAATCCCAGCC

GGTTAAAATGTTCGACCGTCATTCTTCTCTGGCGGGTTGCCAGATTATCAACTACCGTA

CCGACGCGAAACAGAAATGGCTGCTGCTGACTGGCATTTCCGCACAGCAGAACCGCGTG

GTTGGTGCAATGCAGCTGTACTCTGTGGACCGTAAGGTGTCTCAGCCGATCGAAGGTCA

CGCTGCGTCCTTTGCGCAGTTCAAGATGGAGGGTAACGCGGAAGAATCCACCCTGTTTT

GCTTTGCGGTGCGTGGCCAGGCGGGTGGTAAACTGCATATTATCGAGGTTGGCACTCCG

CCGACCGGCAACCAGCCGTTCCCGAAAAAAGCGGTTGACGTTTTCTTTCCGCCGGAAGC

TCAGAACGACTTCCCGGTTGCGATGCAGATTAGCGAGAAACACGACGTGGTTTTCCTGA

TTACCAAGTACGGCTACATCCACCTGTACGACCTGGAGACTGGcACCTGCATCTATATG

AACCGTATCTCTGGTGAAACCATCTTCGTTACTGCTCCGCATGAGGCGACCGCtGGTAT

CATCGGTGTTAACCGTAAAGGTCAGGTGCTGTCTGTTTGTGTTGAGGAAGAGAACATCA

TCCCGTACATCACTAACGTTCTGCAaAACCCGGACCTGGCGCTGCGCATGGCGGTTCGC

AACAACCTGGCAGGCGCTGAGGAGCTGTTCGCGCGTAAATTCAACGCGCTGTTTGCTCA

GGGCAACTATTCTGAAGCGGCGAAAGTTGCTGCAAACGCGCCGAAAGGCATCCTGCGTA

CTCCGGACACCATCCGCCGTTTCCAGTCCGTGCCGGCGCAGCCGGGTCAGACCTCCCCG

CTGCTGCAaTATTTTGGTATCCTGCTGGACCAGGGTCAGCTGAACAAGTATGAAAGCCT

GGAACTGTGCCGTCCGGTGCTGCAaCAGGGCCGTAAACAGCTGCTGGAGAAGTGGCTGA

AGGAAGACAAACTGGAATGCTCCGAAGAGCTGGGTGACCTGGTTAAATCCGTGGACCCG

ACTCTGGCACTGAGCGTGTATCTGCGTGCGAACGTGCCGAACAAAGTTATCCAGTGCTT

CGCGGAAACCGGCCAGGTGCAGAAGATTGTTCTGTACGCAAAAAAAGTTGGCTATACCC

CGGATTGGATCTTTCTGCTGCGTAACGTGATGCGTATCAGCCCGGATCAGGGCCAGCAG

TTTGCACAGATGCTGGTTCAGGACGAGGAGCCGCTGGCGGACATTACCCAGATCGTTGA

TGTTTTTATGGAATATAACCTGATTCAGCAGTGTACTGCGTTCCTGCTGGATGCTCTGA

AAAACAACCGTCCGTCTGAGGGTCCGCTGCAaACTCGTCTGCTGGAAATGAACCTGATG

CACGCGCCGCAGGTGGCAGATGCAATTCTGGGCAACCAGATGTTCACTCACTATGACCG

CGCTCATATCGCGCAGCTGTGCGAAAAAGCGGGTCTGCTGCAaCGTGCGCTGGAGCATT

TCACCGACCTGTACGACATTAAGCGTGCTGTGGTGCATACTCATCTGCTGAACCCGGAA

TGGCTGGTTAACTATTTCGGTTCTCTGAGCGTGGAAGACTCCCTGGAGTGCCTGCGCGC

GATGCTGTCCGCAAACATCCGTCAGAACCTGCAaATTTGTGTTCAGGTGGCTTCTAAAT

ACCATGAACAGCTGAGCACCCAGTCTCTGATTGAGCTGTTTGAATCTTTCAAGTCCTTC

```
GAGGGCCTGTTCTACTTCCTGGGTTCTATCGTGAACTTCTCTCAGGAcCCGGACGTTCA

TTTCAAATACATTCAGGCTGCGTGCAAAACtGGTCAGATCAAAGAAGTGGAACGTATCT

GCCGCGAATCTAACTGCTACGACCCGGAGCGCGTGAAGAACTTTCTGAAAGAAGCGAAG

CTGACCGACCAGCTGCCGCTGATCATCGTTTGTGACCGTTTCGACTTCGTTCATGATCT

GGTGCTGTACCTGTATCGTAACAACCTGCAaAAGTACATTGAGATtTACGTTCAGAAGG

TGAACCCGTCTCGTCTGCCGGTGGTTATTGGTGGCCTGCTGGATGTGGACTGCTCTGAA

GACGTTATCAAAAACCTGATCCTGGTTGTTCGTGGCCAGTTCTCCACCGATGAACTGGT

GGCTGAGGTTGAAAAGCGTAACCGTCTGAAACTGCTGCTGCCGTGGCTGGAAGCGCGTA

TCCACGAAGGTTGTGAGGAACCGGCGACCCATAACGCGCTGGCGAAAATCTATATCGAC

TCTAACAACAACCCGGAACGCTTCCTGCGTGAAAACCCGTATTACGACTCTCGTGTTGT

GGGTAAATACTGTGAGAAACGTGATCCGCACCTGGCGTGTGTTGCGTACGAACGTGGTC

AGTGCGACCTGGAACTGATCAACGTTTGTAACGAAAACTCTCTGTTCAAATCTCTGTCT

CGTTACCTGGTGCGTCGCAAAGATCCGGAGCTGTGGGGTAGCGTTCTGCTGGAATCCAA

CCCGTACCGTCGTCCGCTGATTGACCAGGTGGTTCAGACTGCGCTGAGCGAGACTCAGG

ACCCGGAGGAAGTTAGCGTTACCGTTAAAGCATTCATGACTGCgGACCTGCCGAACGA

GCTGATCGAGCTGCTGGAGAAAATTGTTCTGGACAACTCCGTTTTTAGCGAACACCGCA

ACCTGCAaAACCTGCTGATTCTGACTGCGATCAAGGCGGATCGTACCCGCGTGATGGAA

TATATCAACCGCCTGGATAACTATGATGCGCCGGACATCGCGAACATCGCTATCTCTAA

CGAACTGTTCGAAGAAGCTTTTGCGATTTTCCGTAAATTCGACGTTAACACCTCTGCGG

TGCAGGTGCTGATCGAACATATCGGTAACCTGGACCGTGCGTATGAGTTCGCAGAGCGC

TGCAACGAGCCGGCAGTTTGGTCCCAGCTGGCAAAGGCTCAGCTGCAaAAGGGTATGGT

TAAAGAAGCAATCGACTCTTACATCAAAGCGGATGATCCGTCTAGCTATATGGAAGTTG

TGCAGGCAGCGAACACCTCCGGTAACTGGGAGGAGCTGGTGAAGTACCTGCAaATGG

CGCGCAAAAAGGCGCGTGAATCTTATGTGGAGACCGAGCTGATTTTCGCGCTGGCGAAA

ACCAACCGCCTGGCGGAACTGGAGGAGTTTATCAACGGTCCGAACAACGCTCATATCCA

GCAGGTTGGCGATCGTTGCTACGACGAAAAAATGTACGACGCGGCGAAGCTGCTGTACA

ACAACGTTTCTAACTTCGGCCGTCTGGCTTCTACTCTGGTGCATCTGGGCGAGTATCAG

GCTGCGGTGGACGGTGCGCGTAAAGCGAACTCTACCCGCACTTGGAAAGAAGTTTGCTT

CGCGTGTGTTGACGGCAAAGAATTTCGTCTGGCGCAGATGTGCGGTCTGCACATTGTGG

TGCACGCTGACGAGCTGGAAGAGCTGATCAACTACTATCAGGATCGTGGTTACTTTGAA

GAACTGATCACCATGCTGGAGGCGGCACTGGGTCTGGAACGTGCTCACATGGGTATG

TTCACCGAACTGGCAATCCTGTACTCTAAATTCAAGCCGCAGAAAATGCGCGAGCACCT

GGAACTGTTTTGGAGCCGCGTTAACATCCCGAAGGTTCTGCGTGCGGCGGAGCAGGCGC

ATCTGTGGGCTGAACTGGTGTTTCTGTATGATAAGTATGAGGAATATGACAACGCGATT

ATCACTATGATGAACCATCCGACCGACGCGTGGAAGGAAGGTCAGTTTAAGGACATCAT

CACTAAAGTGGCGAACGTGGAGCTGTACTACCGTGCGATCCAGTTTTACCTGGAGTTCA

AACCGCTGCTGCTGAACGATCTGCTGATGGTGCTGTCTCCGCGTCTGGACCACACCCGT

GCTGTGAACTACTTCTCTAAGGTTAAACAGCTGCCGCTGGTTAAGCCGTATCTGCGTAG

CGTTCAGAACCATAACAACAAGAGCGTGAACGAATCCCTGAACAACCTGTTCATTACCG

AAGAAGACTACCAGGCACTGCGTACCTCTATCGATGCTTACGACAACTTTGATAACATC

TCTCTGGCACAGCGCCTGGAAAAACATGAACTGATTGAGTTCCGTCGCATCGCGGCTTA
```

-continued

```
TCTGTTCAAGGGCAACAACCGTTGGAAACAGTCTGTTGAGCTGTGCAAAAAGATTCTC

TGTATAAAGATGCAATGCAGTACGCGTCCGAATCTAAAGACACTGAGCTGGCTGAGGAA

CTGCTGCAaTGGTTCCTGCAaGAGGAGAAGCGCGAGTGCTTCGGTGCTTGCCTGTTTAC

TTGCTATGACCTGCTGCGTCCGGATGTTGTTCTGGAAACTGCTTGGCGTCATAACATTA

TGGACTTTGCGATGCCGTACTTTATCCAGGTTATGAAAGAATATCTGACCAAAGTGGAC

AAGCTGGACGCGAGCGAAAGCCTGCGCAAGGAGGAAGAACAGGCTACCGAAACCCAGCC

GATCGTGTACGGTAACCTGTCTCTG
```

Figure 4:
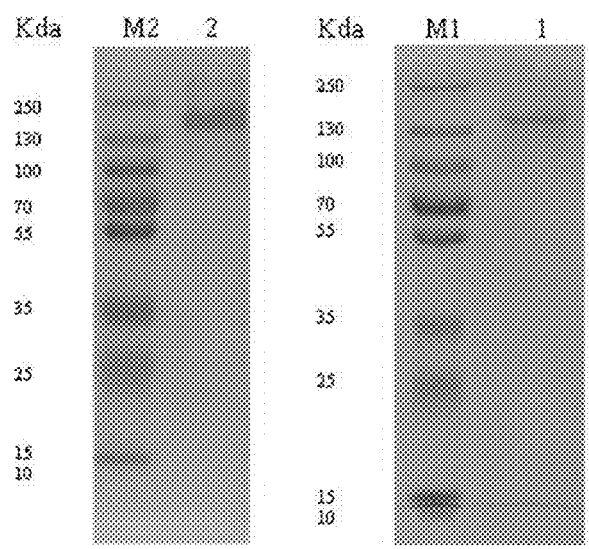
FIG. 4 depicts the results of gel electrophoresis of the cloned clathrin heavy chain (M1: SDS-PAGE Protein Marker; Lane 1: PE1130119-1 protein; M2: Western-Blot Protein Marker; Lane 2: PE1130119-1 protein (using anti-6His antibody ("6His" disclosed as SEQ ID NO: 7))).

The preparation yielded a protein with the following characteristics:

| | |
|---|---|
| Protein Description: | 1) 22.4 mg, >85%, soluble protein with 6His tag (SEQ ID NO: 7) from E. coli;<br>2) QC by SDS-PAGE and Western-Blot. |
| Protein Concentration: | 0.8 mg/mL, as determined by Bradford protein assay with BSA as a standard. |
| Final Prep: | Fusion protein: 22.4 mg; 1.0 mL/vial; 28 vials. |
| Purity: | >85% as estimated by a Coomassie blue-stained SDS-PAGE gel |
| Storage Buffer: | 20 mM Tris.HCl, pH 7.5, 20% Glycerol |
| Storage: | Immediate Storage at −20 C. upon receiving;<br>At first use, aliquot and store at −20 C. to avoid multiple freeze- |
| Intended Use: | This product is intended for research use only. It is not for any human or animal diagnostic and therapeutic use. |
| Isoelectric Point | 5.67 |
| Molecular Weight | 188,955 Da |
| Quality Assurance (see FIG. 4) | M1: SDS-PAGE Protein Marker<br>Lane 1: PE1130119-1 protein<br>M2: Western-Blot Protein Marker<br>Lane 2: PE1130119-1 protein (using anti-6His antibody ("6His" disclosed as SEQ ID NO: 7)) |
| Sequence (SEQ ID NO: 3): | (see below) |

```
1 MAQILPIRFQ EHLQLQNLGI NPANIGFSTL TMESDKFICI REKVGEQAQV

VIIDMNDPSN PIRRPISADS AIMNPASKVI FNIEMKSKMK AHTMTDDVTF

WKWISLNTVA LVTDNAVYHW SMEGESQPVK MFDRHSSLAG CQIINYRTDA

81ALKAGKTLQI 161

KQKWLLLTGI SAQQNRVVGA MQLYSVDRKV SQPIEGHAAS FAQFKMEGNA

EESTLFCFAV RGQAGGKLHI IEVGTPPTGN 241

QPFPKKAVDV FFPPEAQNDF PVAMQISEKH DVVFLITKYG YIHLYDLETG

TCIYMNRISG ETIFVTAPHE ATAGIIGVNR 321

KGQVLSVCVE EENIIPYITN VLQNPDLALR MAVRNNLAGA EELFARKFNA

LFAQGNYSEA AKVAANAPKG ILRTPDTIRR 401

FQSVPAQPGQ TSPLLQYFGI LLDQGQLNKY ESLELCRPVL QQGRKQLLEK

WLKEDKLECS EELGDLVKSV DPTLALSVYL 481

RANVPNKVIQ CFAETGQVQK IVLYAKKVGY TPDWIFLLRN VMRISPDQGQ

QFAQMLVQDE EPLADITQIV DVFMEYNLIQ 561
```

```
QCTAFLLDAL KNNRPSEGPL QTRLLEMNLM HAPQVADAIL GNQMFTHYDR

AHIAQLCEKA GLLQRALEHF TDLYDIKRAV                      641

VHTHLLNPEW LVNYFGSLSV EDSLECLRAM LSANIRQNLQ ICVQVASKYH

EQLSTQSLIE LFESFKSFEG LFYFLGSIVN                      721

FSQDPDVHFK YIQAACKTGQ IKEVERICRE SNCYDPERVK NFLKEAKLTD

QLPLIIVCDR FDFVHDLVLY LYRNNLQKYI                      801

EIYVQKVNPS RLPVVIGGLL DVDCSEDVIK NLILVVRGQF STDELVAEVE

KRNRLKLLLP WLEARIHEGC EEPATHNALA                      881

KIYIDSNNNP ERFLRENPYY DSRVVGKYCE KRDPHLACVA YERGQCDLEL

INVCNENSLF KSLSRYLVRR KDPELWGSVL                      961

LESNPYRRPL IDQVVQTALS ETQDPEEVSV TVKAFMTADL PNELIELLEK

IVLDNSVFSE HRNLQNLLIL TAIKADRTRV                     1041

MEYINRLDNY DAPDIANIAI SNELFEEAFA IFRKFDVNTS AVQVLIEHIG

NLDRAYEFAE RCNEPAVWSQ LAKAQLQKGM                     1121

VKEAIDSYIK ADDPSSYMEV VQAANTSGNW EELVKYLQMA RKKARESYVE

TELIFALAKT NRLAELEEFI NGPNNAHIQQ                     1201

VGDRCYDEKM YDAAKLLYNN VSNFGRLAST LVHLGEYQAA VDGARKANST

RTWKEVCFAC VDGKEFRLAQ MCGLHIVVHA                     1281

DELEELINYY QDRGYFEELI TMLEAALGLE RAHMGMFTEL AILYSKFKPQ

KMREHLELFW SRVNIPKVLR AAEQAHLWAE                     1361

LVFLYDKYEE YDNAIITMMN HPTDAWKEGQ FKDIITKVAN VELYYRAIQF

YLEFKPLLLN DLLMVLSPRL DHTRAVNYFS                     1441

KVKQLPLVKP YLRSVQNHNN KSVNESLNNL FITEEDYQAL RTSIDAYDNF

DNISLAQRLE KHELIEFRRI AAYLFKGNNR                     1521

WKQSVELCKK DSLYKDAMQY ASESKDTELA EELLQWFLQE EKRECFGACL

FTCYDLLRPD VVLETAWRHN IMDFAMPYFI                     1601

QVMKEYLTKV DKLDASESLR KEEEQATETQ PIVYGNLSLL EHHHHHH
```

Example 2—Expression of Clathrin Light Chain

Clathrin light chain (below) was expressed in *E. coli*:

```
(SEQ ID NO: 4):
MAELDPFGAPAGAPGGPALGNGVAGAGEEDPAAAFLAQQESEIAGIENDEAFAILDGGA

PGPQPHGEPPGGPDAVDGVMNGEYYQESNGPTDSYAAISQVDRLQSEPESIRKWREEQM

ERLEALDANSRKQEAEWKEKAIKELEEWYARQDEQLQKTKANNRVADEAFYKQPFADVI

GYVTNINHPCYSLEQAAEEAFVNDIDESSPGTEWERVARLCDFNPKSSKQAKDVSRMRS

VLISLKQAPLVH (SEQ ID NO: 5):
ATGGCGGAACTGGACCCGTTCGGCGCTCCGGCAGGCGCACCGGGCGGTCCGGCGCTGGG

TAACGGCGTTGCGGGTGCTGGTGAAGAAGACCCGGCAGCAGCGTTCCTGGCGCAGCAGG

AATCTGAAATCGCAGGTATCGAAAACGATGAAGCGTTCGCGATCCTGGACGGTGGTGCT
```

```
CCGGGTCCGCAGCCGCACGGTGAACCGCCGGGTGGTCCGGATGCGGTTGACGGTGTTAT

GAACGGCGAGTACTACCAGGAGTCTAACGGTCCGACCGATTCTTACGCGGCAATTAGCC

AGGTTGATCGTCTGCAaTCCGAACCGGAATCTATCCGTAAATGGCGTGAGGAGCAGATG

GAACGCCTGGAAGCTCTGGACGCGAACTCTCGCAAACAGGAGGCGGAATGGAAAGAAAA

AGCGATCAAAGAGCTGGAAGAATGGTATGCGCGTCAGGACGAACAGCTGCAaAAAACCA

AAGCGAACAACCGTGTGGCGGACGAAGCATTCTACAAACAGCCGTTTGCGGACGTTATC

GGTTACGTTACCAACATCAACCATCCGTGCTACTCTCTGGAGCAGGCAGCGGAAGAAGC gTTCGTGAACGACATCGACGAATCTAGCCCaGGcACCGAATGGGAACGTGTTGCGCGCC

TGTGCGACTTCAACCCGAAATCTTCTAAACAGGCTAAAGACGTTTCTCGTATGCGTTCT

GTTCTGATCTCTCTGAAGCAGGCTCCGCTGGTTCAC
```

The preparation yielded a protein with the following characteristics:
Protein Description:
12.96 mg, >85%, soluble protein with 6His tag (SEQ ID NO: 7) from *E. coli*;
Protein Concentration:
0.60 mg/mL, as determined by Bradford protein assay with BSA as a standard.
Final Prep:
1.8 mL/tube, 12 tubes
Purity:
>85% as estimated by a Coomassie blue-stained SDS-PAGE gel
Storage Buffer:
50 mM Tris, 150 mM NaCl, 10% Glycerol, pH 8.0
Storage:
Immediate Storage at −20° C. upon receiving
At first use, aliquot and store at −20° C. to avoid multiple freeze-thaws.
Intended Use:
This product is intended for research use only. It is not for any human or animal diagnostic and therapeutic use.

```
ProteinSequence(SEQ ID NO: 6):
  1 MAELDPFGAP AGAPGGPALG NGVAGAGEED PAAAFLAQQE SEIAGIENDE AFAILDGGAP

61 GPQPHGEPPG GPDAVDGVMN GEYYQESNGP TDSYAAISQV DRLQSEPESI RKWREEQMER

121 LEALDANSRK QEAEWKEKAI KELEEWYARQ DEQLQKTKAN NRVADEAFYK QPFADVIGYV

181 TNINHPCYSL EQAAEEAFVN DIDESSPGTE WERVARLCDF NPKSSKQAKD VSRMRSVLIS

241 LKQAPLVHLE HHHHHH
```

Figure 5:
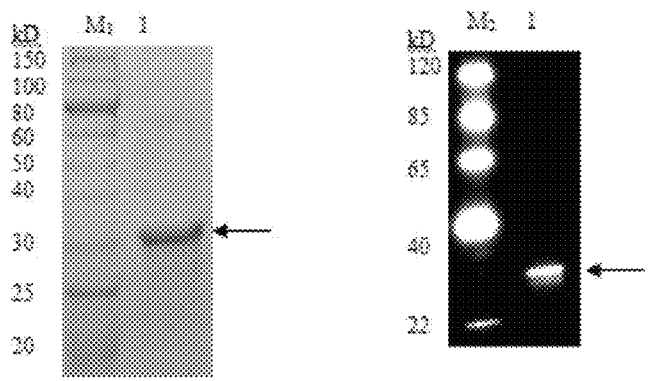
FIG. 5 depicts the results of gel electrophoresis of the cloned clathrin light chain (M1: SDS-PAGE Protein Marker; Lane 1: PE1130119-2 protein; M2: Western-Blot Protein-Marker; Lane 2: PE1130119-2 protein (using anti-6His antibody ("6His" disclosed as SEQ ID NO: 7))).

Protein Length
256
MW
28136.9
Predicted pI
4.37
Quality Assurance (see FIG. 5):
M1: SDS-PAGE Protein Marker
Lane 1: PE1130119-2 protein
M2: Western-Blot ProteinMarker
Lane 2: PE1130119-2 protein (using Anti-6His antibody ("6His" disclosed as SEQ ID NO: 7))

Example 3—Loading of Self-Assembled Protein

The self-assembled protein was loaded with a fluorescent compound to assess its ability to self-assembling following loading.

Recombinant clathrin heavy chain (HC) and light chain (LC) were diluted at 300 µg/mL and 800 µL/mL, respectively in 10 mM Tris-HCl (pH 7.9). A fluoresceinated test compound (FTC) was diluted at 500 µg/mL in the same buffer. Assembly of 100 µL in a 96-well assay plate was initiated by adding 4 µL of 1 M 2-(N-morpholino)ethane-sulfonic acid (MES) buffer, pH 6.5 supplemented with 10 mM ethylene glycol tetraacetic acid (EGTA) and 75 mM CaCl$_2$. A control was used with pH 7 MES buffer. OD320 nm readings were measured using the SpectraMax M3 (molecular devices) and the results were plotted by the software provided by the equipment.

Example 4—Loading of Self-Assembled Protein (Prophetic)

A variety of ratios of HC, LC, and FTC, as well as low pH, are being tested in order to investigate assembling efficiency.

Other experiments to study drug loading are being tested.
1. Load or attach the drug to the light chain assembly cage and then load the loaded light chain to the heavy chain in self-assembling conditions (indirect loading to the main cage). The light chain may increase the stability of the main heavy chain cage.
2. Use direct mixing of drug and cages to change drug loading under different open and self-assembling conditions.
3. Use different size drugs, such as paclitaxel or gemcitabine.

Example 5—Animal Studies (Prophetic)

Compare efficacy of loaded vehicles to efficacy of drugs alone in animal models.
Perform acute and chronic toxicity studies in two animal species with the lead drug.

Example 6—Co-Administration of a First Composition and a Second Composition to Enhance Immunogenic Response (Prophetic)

Co-administration of a first composition (comprising a first self-assembled clathrin vehicle, an anti-cancer agent, and a targeting agent) with a second composition (comprising a second self-assembled clathrin vehicle and an anti-PD-1 antibody) is expected to provide enhanced therapeutic effect as compared to the first composition alone, the second composition alone, and the additive effect of the first composition and the second composition. The second composition may further comprise an immunogen payload.

REFERENCES

All publications and patents mentioned herein, including those items listed below, are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification.

---

We claim:

1. A composition comprising a clathrin light chain covalently conjugated to an anti-cancer agent, wherein the anti-cancer agent is selected from paclitaxel, gemcitabine, azonafide, colcemid, colchicine, vinblastine and vincristine, wherein the clathrin light chain comprises SEQ ID NO: 4, wherein the composition does not comprise a clathrin heavy chain, and wherein the composition does not comprise any targeting agent.

2. The composition of claim 1, wherein anti-cancer agent is paclitaxel, gemcitabine, or an azonafide.

3. The composition of claim 1, wherein the anti-cancer agent is colcemid, colchicine, paclitaxel, vinblastine or vincristine.

4. The composition of claim 1, wherein the anti-cancer agent is covalently conjugated to the clathrin light chain via a crosslinking agent.

5. A method of treating cancer in a subject in need thereof, comprising:
administering to the subject a therapeutically effective amount of the composition of claim 1.

6. The method of claim 5, wherein the cancer is lung cancer or pancreatic cancer.

7. The method of claim 5, wherein the anti-cancer agent is paclitaxel, gemcitabine, or an azonafide.

8. The method of claim 5, wherein the anti-cancer agent is covalently conjugated to the protein light chain via a crosslinking agent.

* * * * *